(12) United States Patent
Laufer

(10) Patent No.: US 6,853,452 B1
(45) Date of Patent: Feb. 8, 2005

(54) PASSIVE REMOTE SENSOR OF CHEMICALS

(75) Inventor: Gabriel Laufer, Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 0 days.

(21) Appl. No.: 09/936,833

(22) PCT Filed: Feb. 18, 2000

(86) PCT No.: PCT/US00/04027

§ 371 (c)(1),
(2), (4) Date: Sep. 17, 2001

(87) PCT Pub. No.: WO00/55602

PCT Pub. Date: Sep. 21, 2000

Related U.S. Application Data
(60) Provisional application No. 60/125,686, filed on Mar. 23, 1999, and provisional application No. 60/124,755, filed on Mar. 17, 1999.

(51) Int. Cl.[7] .............................................. G01N 21/00
(52) U.S. Cl. ...................................... 356/436; 356/438
(58) Field of Search ............................... 358/436–440; 73/23.2; 250/343, 339.13, 345

(56) References Cited

U.S. PATENT DOCUMENTS

| | | | |
|---|---|---|---|
| 3,955,891 A | 5/1976 | Knight et al. | |
| 4,790,654 A | 12/1988 | Clarke | |
| 5,128,797 A | 7/1992 | Sachse et al. | |
| 5,479,258 A | 12/1995 | Hinnrichs et al. | |
| 5,886,247 A | * 3/1999 | Rabbett | 73/23.2 |
| 5,905,571 A | 5/1999 | Butler et al. | |
| 6,010,665 A | 1/2000 | Dosoretz et al. | |
| 6,064,488 A | * 5/2000 | Brand et al. | 356/440 |

OTHER PUBLICATIONS

Higdon, et al., Air Force Research Laboratory Long–Range Airborne CO2 DIAL Chemical Detection System, Proc. 19th International Laser Radar Conference, 651–654, (1998).

Hewish, Detection and Protection: what you don't know can kill you, Janes International Defense Review, No. 30–48, (1997).

Rossberg, Silicon Micromachined Infrared Sensor with Tunable Wavelength Selectivity for Application in Infrared Spectroscopy, Sensors and Actuators A, 46–47, 413–416, 1995.

Herget, et al., IR GFCR Instrument for In–Situ Measurement of Gaseous Pollutant Concentration, App. Opt. 15, 1222–1228, (1976).

Althouse, et al., Chemical vapor detection with a multispectral thermal imager, Opt. Eng., 30, 1725–1733, 1991.

Wimmers, et al., Focal Plane Arrays: Better, Smaller IR Imagers for New Applications, The Photonics Design and Applications Handbook, H–212–217, 1997.

(List continued on next page.)

Primary Examiner—Michael P. Stafira
(74) Attorney, Agent, or Firm—Robert J. Decker

(57) ABSTRACT

A remote sensor for use as a handheld, mobile or stand-alone sensor has first (12) and second (16) optical paths, light collecting optics, a sample filter (10) assembly positioned in a first optical Path (12), a reference filter (14) assembly positioned in a second optical path (16), a detector assembly to detect the filtered light r other radiation, and a detector output comparison device such as BRD to minimize the effects of common background noise components, differences in light or other radiation source power, and absorption or emission by interfering species.

62 Claims, 7 Drawing Sheets

OTHER PUBLICATIONS

Lopez, et al., Multispectral interference filters and their application to the design of compact non–dispersive infrared gas analysers for pollution control, Sensors and Actuators A, 37–38, 502–506, 1993.

Ronald Highland et al., Laser Long–Range Remote Sensing Program Experimental Results, SPIE Proceedings vol. 2508, 30–37, (1995).

Larry Grim, et al., Evaluation of Passive FTIR Algorithms, Proc. Of the 3rd Workshop on Stand–Off Detection for Chemical and Biological Defense, pp. 251–258, 1994.

James O. Jensen, Chemical Imaging Sensor, Chemical/Biological Mission Area Advanced Planning Briefing for Industrty, Johns Hopkins APL, Apr. 1–2, (1998).

Photonics Spectra, p. 42, Feb. 1999.

Dennis R. Suhre, et al., Imaging Spectroradiometer for the 8–12 mm Region with a 3 cm Passband Acousto–Optic Tunable Filter, Applied Optic, vol. 37, No.12, pp. 2340–2345, Apr. 20, 1998.

C. B. Ludwig, et al., Measurement of Air Pollutants from Satellites. 1: Feasibility Considerations, Applied Optics, vol. 13, No. 6, pp. 1494–1509, Jun. 1974.

T. V. Ward, et al., Gas Cell Correlation Spectrometer: GASPEC, Applied Optics, vol. 14 No. 12, pp. 2896–2904, Dec. 1975.

Henry G. Reichle, Jr. et al., Middle and Upper Tropospheric Carbon Monoxide Mixing Ratios as Measured by a Satellite–Borne Remote Sensor During Nov. 1981, J. Geophys. Res., 91, pp. 10.865–10.887, (1986).

Glen W. Sachse, et al., Geo–Stationary Imaging of Atmospheric CO and CH4 Distributions: Instrument Concept, Paper OWC7–1, OSA Topical Meeting on Optical Remote Sensing of the Atmosphere, Santa Fe, NM, Feb. 10–14, (1997).

Glen W. Sachse, et al., Demonstration of a New GFCR Method with CH4 Measurements at 2.3 microns, presented at Conference at the Optical Remote Sensing of the Atmosphere Sixth Topical Meeting, Salt Lake City, Mar. 8–12, 1993.

D. C. Senft, et al., Chemical Detection Results from Ground Tests of an Airborne CO2 Differential Absorption Lidar System, pp. 657–660.

William Suliga, et al., Short Range Biological Standoff Detection System (SR–BSDS) Fourth Joint Workshop on Standoff Detection for Chemical and Biological Defense, pp. 265–274.

Christopher M. Gittins, et al., A Frequency Agile Bandpass Filter for Direct Detection Lidar Receivers, Fourth Joint Workshop on Standoff Detection for Chemical and Biological Defense, pp. 71–83.

Dennis F. Flanigan, Vapor–detection sensitivity as a function of spectral resolution for a single Lorentzian band, Applied Optics, vol. 34, No.15, pp. 2636–2639, May 20, 1995.

Rajarshi Roy, Laser Noise, SPIE, vol. 1376, pp. 219–221, 1990.

Robert A. Marsland, Balanced photoreceivers challenge shot–noise limit, Laser Focus World, pp. S41–S45, Mar. 1994.

David M. Sonnenfroh, et al., Ultrasensitive, visible tunable diode laser detection on NO2, Applied Optics, vol. 35, No. 21, pp. 4053–4058, Jul. 20, 1996.

* cited by examiner

PASSIVE REMOTE SENSOR OF CHEMICALS

CROSS-REFERENCE TO RELATED PROVISIONAL APPLICATIONS

The present application is a national stage filing of International Application No. PCT/US00/04027, filed Feb. 18, 2000, which claims benefit under 35 U.S.C. Section 119(e) from U.S. Provisional Patent Applications Ser. Nos. 60/124,755, filed Mar. 17, 1999 and 60/125,686, filed Mar. 23, 1999, of which are incorporated by reference herein in their entireties.

FIELD OF THE INVENTION

The present invention relates to a passive, remote device and method for detecting chemicals. More particularly, the present invention relates to a passive, remote device and method using differential absorption radiometer (DAR) or notch filter correlation radiometer (NFCR) technology to detect chemicals including gases, liquids, solids and adsorbents.

BACKGROUND OF THE INVENTION

There is an ongoing need for devices and methods capable of the early, passive remote detection of dangerous gases and other substances. Recently, the need for such systems has been heightened by the spread of chemical warfare technology around the world and the increasing number of acts of global terrorism. Indeed, the potential release of dangerous substances is now a serious concern not only for the military, but for local governments as well.

The development of passive remote detectors has also been driven by other factors, such as the growing concern for the effects of industrial and vehicular emissions as well as other forms of environmental pollution such as that resulting from the use of pesticides. Remote detectors are also needed to monitor and study trends in environmental conditions in order that their causes may be understood and addressed, as well as to identify and provide warnings regarding day-to-day conditions that may affect the health of local and global populations.

Passive remote detectors of chemicals in gaseous forms primarily in the atmosphere ideally operate in the 8–13.3 $\mu$m spectral range, where (a) many objects and gases at a standard temperature of about 25° C. have strong infrared (IR) emissions; (b) the atmosphere is relatively transparent over long distances; and (c) many target species have strong absorption (or emission) depending on their temperatures relative to their background features. Although the 3–5 $\mu$m spectral range may offer advantages (b) and (c), objects and gases at standard temperature do not emit significant radiation. Accordingly, a remote detector generally may effectively operate in the 3–5 $\mu$m spectral range only where alternative radiation sources such as the sun or an artificial light are available.

In the past, several types of in situ and standoff, or remote, sensor systems have been proposed. Two prominent in situ systems presently being marketed are the Chemical Agent Monitor (CAM) and the Enhanced CAM (ECAM), both of which are manufactured by Graseby Dynamics Ltd. of the United Kingdom and operate on the principle of ion mobility. Both systems are portable, with the ECAM being designed as a handheld sensor. These systems require continuous sampling of the atmosphere at the point of measurement, and therefore can detect a target gas only if the sensor is immersed in it. This is an undesirable limitation, and can be dangerous if the target gas is toxic. In addition, these systems are only capable of taking measurements in a point-wise fashion, such that numerous measurements are required to determine the boundaries of a chemical cloud.

Another commercially available system is the surface acoustic wave (SAW) minicad. The SAW system is also portable and offers the exceptionally high sensitivity of 0.2 mg/m$^3$, but lacks specificity and cannot determine the specific identity of a gas (i.e., it can only determine any of a certain number of gases may be present). Yet another in-situ system has been proposed using a planar optical waveguide chip with 13 interferometric sensors built onto it. See "Photonic Spectra," February, 1999, at 42. The device detects changes in the optical index of refraction of certain films that are deposited on it. These changes occur when the target gas for which each of the films is sensitive is absorbed by the films. The system permits detection of 100 parts per billion of benzene, toluene and xylene, all toxic chemicals. Like the CAM, this device is an in-situ sensor. In addition, this system can detect only the gases for which absorbing films are available.

Remote detection of chemicals depends mostly on optical techniques, which can be classified into two groups: (a) active techniques such as lidar (light detection and ranging), differential absorption lidar (DIAL), or laser-induced fluorescence (LIF) and (b) passive techniques, such as Fourier transform IR spectroscopy (FTIR), or multi or hyper spetral techniques such as gas filter correlation radiometry (GFCR) or tunable etalons. Several research groups are developing DIAL techniques for detecting chemical agents (CAs) using wavelength-agile $CO_2$ lasers. For example, a laser airborne remote sensing (LARS) system under development by the United States Air Force has demonstrated slant path detection capabilities of atmospheric parameters from a distance of 21 km (see Highland et al., "Laser Long-Range Remote Sensing Program Experimental Results," SPIE Proceedings, vol. 2580(1995) at 30–37) and exceptional on-ground testing detectivity of $SF_6$ and $NH_3$ at a distance of 2 km (see Higdon, et at., "Air Force Research Laboratory Long-Range Airborne $CO_2$ DIAL Chemical Detection System," Proc. 19$^{th}$ International Laser Radar Conference (1998) at 651–54; Senft, et al., "Chemical Detection Results From Ground Tests of an Airborne CO2 Differential Absorption Lidar System," Proc. 19$^{th}$ International Laser Radar Conference (1998) at 657–60). Projected slant-path range of the system is 30 km. The DIAL and other lidar systems suffer from, among other things, a dependance on a narrowband, rapidly tunable laser system. Consequently, they are extremely complex and expensive, require highly trained personnel for operation, and provide an undesirably limited field of view (FOV) (which is delimited in such systems by the divergence of the laser beam). In addition to these disadvantages, the filter and detector components of the Air Force's LARS $CO_2$ DIAL system must be cooled in a liquid nitrogen environment.

Typical LIF systems, like DIAL systems, include a tunable-wavelength laser and a large aperture telescope and detector system. Unlike DIAL systems, however, the signal in LIF systems is emitted by the fluorescence of the target species which is excited by the laser. Accordingly, the signal is weaker than that of the DIAL systems and the range is limited. On the other hand, the ability of LIF systems to reject fluorescence signals from unwanted background and scattered signals, and therefore the specificity of such systems, is superior to that of DIAL systems. LIF systems are generally used for detection of biological species. See Suliga, et al., "U.S. Army Chemical and Biological Defense Command's Short Range Biological Standoff Detection System (SR-BSDS)," Joint Workshop on Standoff Detection for Chemical and Biological Defense, Williamsburg, Va. (Oct. 26–30 1998), at 265–74.

A survey of passive remote sensors is provided in Hewish, "Detection and Protection: What You Don't Know Can Kill You," Janes International Defense Review (1997) at 30–48. Perhaps the most notable currently available passive sensor is the M21 Remote Sensing Chemical Agent Alarm (RSCAAL) This system has already been fielded and is based on a FTIR technology. It can detect clouds of toxic agents from distances of up to 5 km with excellent sensitivity when the temperature difference between the gas and its surroundings is 4° K., and at a lesser sensitivity when the temperature difference is lower. The main disadvantage of FTIR systems, including the RSCAAL system, is that they depend on a complete spectral scan followed by detailed analysis of the spectrum. To accomplish that scan, the system requires a complex, highly refined mechanical tunning arrangement which is difficult to make sufficiently rugged for field applications. Operating such a complex system and analyzing its detailed output requires highly trained personnel. Furthermore, because the system covers essentially the entire spectrum, the radiation available at each spectral location is only fraction of the radiation collected during the time of the entire scan.

In remote sensor systems, hyperspectral or multispectral imaging techniques may be employed to provide an imaging capability. In hyperspectral imaging spectroscopy, spectrally and spatially resolved information is acquired to provide a two dimensional image of the distribution of chemicals targeted for detection. Hyperspectral images may be obtained by an imaging spectrometer, in which case a narrow strip in the FOV is imaged onto the front slit of the spectrometer. The dispersive element in the spectrometer creates a full spectrum for each point of the imaged line, thereby forming a two-dimensional pattern (wavelength vs. linear spatial position), which is recorded by a focal plane array (FPA) in the back plane of the spectrometer. A full hyperspectral data cube may be obtained by imaging additional strips in the FOV while recording the point-by-point spectral distribution. Alternatively, the data cube may be divided into spectral "slices," i.e., the two-dimensional FOV may be viewed through a tunable bandpass filter that transmits one color at a time. Monochromatic images of the two-dimensional object are recorded sequentially to obtain a stack of images of the same object—each at a different wavelength.

Hyperspectral techniques may require up to 200 such images covering a wide spectral range. Multispectral techniques, on the other hand, typically cover 20 spectral slices per object. Undoubtedly, systems employing hyperspectral techniques may provide greater spectroscopic detail and therefore have higher specificity (i.e., the ability to reject interferences by species that are not targeted for detection). However, they also require longer scans and much larger data storage and processing capabilities than multispectral-based systems, and therefore are less useful for operation by untrained personnel or from fast moving platforms.

Several hyperspectral and multispectral imaging techniques for the remote detection of chemicals have been proposed. One of the truly hyperspectral detection techniques includes the use of a tunable acousto-optic filter (AOTF) for the 8–12 $\mu$m range at a bandwidth of 3 cm$^{-1}$. See Suhre, et al., "Imaging Spectroradiometer for the 8–12 $\mu$m Region with a 3 cm$^{-1}$ Passband Acousto-Optic Tunable Filter," Appl. Opt., vol. 37, no. 12 (1998) at 2340–45. But biasing the acousto-optic element during the tuning process causes the image to shift slightly, thereby complicating correlation between images obtained at different wavelengths. A separate technique using a tunable Fabry-Perot etalon is also being developed for hyperspectral imaging of chemical agents. See Rossberg, "Silicon Micromachined Infrared Sensor with Tunable Wavelength Selectivity for Application in Infrared Spectroscopy," Sensors and Actuators A 46–47 (1995) at 413–16. However, fielding a Fabry-Perot filter is complicated by the need for good alignment and spacing control between the moving mirrors. Finally, it has been proposed to use a diffractive lens as a tunable element for gaseous chemical imaging. See U.S. Pat. No. 5,479,258, issued Dec. 26, 1995 to Hinnrichs, et al., which is incorporated by reference herein in its entirety. But cross talk between its spectral images can compromise its specificity.

All three hyperspectral techniques discussed here offer the potential of high spectral resolution, broad spectral scanning capabilities and excellent radiative throughput. However, to benefit from these potential advantages, a full set of images, each at a separate wavelength must be recorded. Assuming that these techniques can uniformly provide a bandwidth of 10 cm$^{-1}$, then coverage of the entire 8–13.3 $\mu$m range (1250 to 752 cm$^{-1}$), the range over which many chemicals of interest are spectrally active, will require 42 separate images. The time required to acquire these images is usually limited by the maximum imaging rate of available FPAs, which presently stands at $\leq$50 Hz. Nearly one second will therefore be required to record an entire data cube (or longer when the bandwidth is narrower).

In contrast to hyperspectral imaging techniques, multispectral techniques like those employed by GFCR, DAR or NFCR systems cover only the spectral regions that are needed to detect the selected target species. A typical GFCR includes a sample cell containing a target species, and a reference vacuum cell. The sample cell and reference cell are moved mechanically into and out of the detector FOV. See Herget, et al., "Infrared Gas-Filter Correlation Instrument for In-Situ Measurement of Gaseous Pollutant Concentrations," App. Opt. 15 (1976) at 1222–28. Such systems have been used to monitor smoke stack pollutants such as CO, NO, $SO_2$, HCl, and HF by absorption of radiation from an IR source across that stack. Detection ranges of 10–5000 ppm-m have been achieved for many of these species. An alternative GFCR method for the detection of absorption by trace atmospheric species of natural IR emission, or the emission by the detected gases themselves has been used to sense $CH_4$, $C_2H_6$, HCl, and CO. See Ward, et al., "Gas Cell Correlation Spectrometer: GASPEC," App. Opt., 14 (1975) at 2896–904. The system has been used both in the upward and nadir looking modes through up to 300 m atmospheric paths. The specificity of the system has been demonstrated by showing experimentally that a 1000 ppm-m change in the background burden of $CO_2$ produced the noise equivalent of the detection of 400 ppm-m of CO.

The primary drawback of GFCRs is the need for the sensor to include a cell containing the sample species, which may present a hazard when the sensor is to be used for the detection of toxic chemicals or chemicals that are difficult to handle. In addition, the requirement of a separate cell for each target chemical results in a bulky detector. Moreover, the need to mechanically switch the cells in and out of the FOV significantly reduces system reliability and speed, and may prevent the imaging of proliferated chemicals, such as gas clouds or liquid spills, due to a loss of registration between consecutive images.

U.S. Pat. No. 5,128,797, issued Jul. 7, 1992 to Sachse, et al., which is incorporated by reference herein in its entirety, proposes a non-mechanical GFCR and DAR, which uses optical polarization modulation to switch between the optical paths of the system. See also Wang, et al., "Demonstration of New GFCR Method with CH4 Measurements at 2.3 Microns, Conference of the Optical Remote Sensing of the Atmosphere Sixth Topical Meeting," Salt Lake City, Utah (Mar. 8–12, 1993). Although this approach avoids the unreliability associated with mechanically switching between the cells, it is undesirably complex and expensive, requiring the use of a polarization modulator, two polarization beam-splitters, and a waveplate. In addition, the performance of available polarizing beam splitters in the 8–13.3 $\mu$m spectral range presently is not sufficient to develop a sensitive detector of the design of the '797 patent for use in the 8–13.3 $\mu$m range.

U.S. Pat. No. 5,905,571, issued May 18, 1999 to Butler, et al., which is incorporated by reference herein in its entirety, discloses a new GFCR-like system which uses micro-machined diffraction gratings to produce spectra that are similar to the absorption spectra produced by the sample cells of the GFCR. According to the '571 patent, it may be possible to prepare an array of gratings, each simulating the sample cell of one chemical species. By placing the gratings in front of a single detector, or a detector array, measurements may be produced that are comparable to those of the GFCR itself, but without the inherent disadvantage of using sample cells. While attempting to address this disadvantage, however, the grating-based design of the '571 patent introduces a number of additional disadvantages. Unlike standard GFCR designs, the grating-based GFCR requires that a narrow slit be positioned between the grating and the detector in order to separate radiation directed by the grating that has the desired spectral characteristics from radiation that does not have the desired characteristics. The slit is also used to reduce interferences by stray light, to which the grating-based system is particularly susceptible. Without such a slit, the system loses some of its spectral resolving capabilities. Although the detector itself may be used as a relatively wide slit, the spectral resolution of the system would be significantly reduced. Consequently, the light gathering capability or FOV of the grating-based GFCR system is limited by the slit width. A compromise therefore must be made between two conflicting requirements: a large signal or large FOV that requires a wide slit, or high spectral resolution that requires the slit to be narrow.

The slit required by the design of the '571 patent also prevents the possibility of imaging the spatial distribution of chemical clouds. In addition, because light falling on the gratings must be collimated, whereas light falling on the slit must be focused, the grating-based GFCR must include a train of optical elements consisting of collimating and focusing lenses. Given the optics required, the fact that the system is sensitive to optical alignment between the grating and the slit, and the fact that the system requires sufficient optical path for the proper grating dispersion to develop (which may require up to several centimeters of distance between the grating and slit), the grating-based GFCR system clearly is not capable of miniaturization.

U.S. Pat. No. 3,955,891, issued May 11, 1976 to Knight, et al., which is incorporated by reference herein in its entirety, discloses a similar dispersive-correlation technique. The design of the '891 patent employs a concave grating to disperse the incoming light into its various spectral components, then selects the desired components by placing a spatial filter, shaped to correlate with the pattern formed by the desired spectrum, in the focal plane of the grating. The system has many of the features and disadvantages of the grating-based GFCR. A significant additional disadvantage, however, is that the need for a combination of a concave grating and spatial filter assemblies renders the system complex and cumbersome.

U.S. Pat. No. 4,790,654, issued Dec. 13, 1988 to Clarke, which is incorporated by reference herein in its entirety, discloses an alternative dispersive, multispectral technique which uses an imaging system followed by a cylindrical lens that creates a line focus of an image, which is then projected on a planar diffraction grating. The radiation diffracted from the grating is made of numerous strips, each at a different color and each propagating at a slightly different angle. By intercepting this radiation by a segmented mirror, it is possible to control each color component independently form the others. For example, by controlling the reflectivity of certain mirror segments it is possible to remove from the image selected spectral components. Although the technique of the '654 patent purports to provide well-defined spectral signatures, as well as capabilities of imaging preprogrammed species, it is exceptionally complex and, depends heavily on fine optical alignment which can affect the spectral resolution and the registration between images that are designed to represent the species itself and images that are representative of its background.

Althouse, et al., "Chemical Vapor Detection with a Multispectral Thermal Imager," Opt. Eng., 30 (1991) at 1725–33, disclose a multispectral technique employing a striped filter containing up to eight strips of bandpass optical filters of 0.5 $\mu$m bandwidth (or 35–70 cm$^{-1}$) to cover the 8–13.3 $\mu$m range. This approach is disadvantageous, however, as it depends on an exceptionally broad bandwidth, which results in an undesirably low specificity. This is because the entire spectral range is covered by only eight bandpass filters. In addition, the Althouse, et al. design suffers from undesirably low sensitivity because it fails to recognize the need for a background subtraction and normalization technique. Althouse, et al. recommend the use of cryogenically cooled filters, and the positioning of such filters sufficiently far away from the detector that noise contributions by radiation from the filters themselves will be reduced to acceptable levels.

Wimmers, et al., "Focal Plane Arrays: Better, Smaller IR Images for New Applications," The Photonics Design and Applications Handbook, H-212–217 (1997) discloses a technique for detecting gaseous chemicals in the 3–5 $\mu$m range, using bandpass filters. Four bandpass filters are attached to a four position filter wheel and are spun in front a detector. Typically, each filter is selected to have a transmission band that matches the absorption spectra of certain gas species. By imaging the FOV through such filters, it is possible to obtain images of the gaseous species that have an absorption that matches their corresponding filter transmission. Disadvantageously, the design requires that the filters be cryogenically cooled. In addition, the design does not provide for methods to correct for the effects of background radiation or emission, or absorption by atmospheric or other background species. Furthermore, the use of a mechanical filter wheel to switch between the filters reduces the reliability of the system and prevents miniaturization. In addition, the use of moving filters inherently leads to a loss of registration between the images obtained through the two different filters, thereby preventing the possibility of subtracting one image from the other. The Wimmers, et al. method also does not contemplate correcting for background interferences.

Lopez, et al., "Multispectral Interference Filters and Their Application to the Design of Compact Non-Dispersive Infrared Gas Analaysers for Pollution Control," Sensors and Actuators A, 37–38 (1993) at 502–06, disclose a bandpass filter-based approach that allows simultaneous detection of multiple species. In this technique, a single substrate is coated by multiple refractive layers and then etched to produce numerous bandpass filters each at a different location on the substrate. Preferably, the filter is designed as a linear array of various bandpass filters. The transmission line-center of each filter can be selected to match the absorption or emission of a selected species. By placing the bandpass filter arrangement in front of a linear detector array, simultaneous measurements of the absorption or emission by multiple species may be obtained. However, Lopez, et al. focus solely on filter construction concepts, contemplating only the direct measurement of intensity values. Lopez, et al. do not consider the need to correct for background interference or how such correction would best be accomplished.

Accordingly, there is a need for a sensor that is capable of remotely detecting, and preferably imaging, gaseous, liquid, solid or adsorbed chemicals even when the background, its constituents and its illumination change rapidly. Such a sensor preferably would be sufficiently simple in design to be compact, rugged, inexpensive, and easy to use and interpret by untrained operators. For example, it would be desirable to have a sensor that is sufficiently compact and rugged to be configured and used as a handheld chemical detector, while having a satisfactory sensitivity, specificity, ability to correct for effects of background radiation or emission and absorption by background atmospheric or other species, and a high imaging or spatial resolution. It would also be desirable for such a sensor to be designed alternatively to have a large FOV for large area coverage, and to be sufficiently energy efficient to be useful for long-duration, stand-alone operation. Such a sensor preferably would be capable of detecting, and preferably imaging, gaseous chemicals such as dust, atmospheric effluents, pollution, pesticide vapors, naturally occurring atmospheric gases (e.g., $H_2O$, $CO_2$, $O_3$, $N_2O$, $NO_x$, and CO gases), gas leaks, liquid spills, hydrogen and hydrocarbon fires, surface impurities, plasmas or electric discharges. Such a sensor also preferably would have an exceptionally large signal to noise ratio, thereby permitting the use of uncooled detectors in the IR or smaller imaging lens in handheld applications.

SUMMARY OF THE INVETION

The several shortcomings and disadvantages of conventional remote chemical detection techniques are addressed by the present invention, In general, the sensor of the present invention has a first optical path and a second optical path, light collecting optics configured to collect light or other radiation to be transmitted or emitted along the first and second optical paths, and a sample filter assembly positioned in the first optical path after the light collecting optics. As is described in detail below, the sensor may also include a reference filter assembly positioned in the second optical path after the light collecting optics. One or more detector assemblies may be used to detect the light or other radiation transmitted through the sample and reference filter assemblies, and one or more associated detector output comparison devices are used to compare, and preferably normalize, the sample and reference output signals. In comparing the sample and reference outputs, the output comparison device preferably subtracts one output signal from the other. In normalizing the sample and reference outputs, the output comparison device preferably divides the difference of the sample and reference outputs by the sample output or the reference output.

In one embodiment, both sample and reference filter assemblies are used, and each includes a bandpass filter. The sample bandpass filter may be configured to be capable of transmitting at a radiation frequency that coincides with an absorption or emission line of a target species (preferably a strong absorption or emission line), and the sample bandpass filter may be matched by a reference bandpass filter configured to transmit at a frequency that does not coincide with a spectral line of the target species. Thus, the output of the detector output comparison device will be indicative of the net target species absorption or emission and preferably independent of variations in the overall illumination level. Preferably, when the bandpass frequency of the sample bandpass filter assembly coincides also with an absorption or emission line of a non-target species such as atmospheric $H_2O$, $CO_2$, $O_3$, $N_2O$, $NO_x$, or CO gas, or another gas or aerosol that may be found in the atmosphere, the reference bandpass filter assembly is configured to transmit at a frequency that coincides with the spectral line of the non-target species transmitted by the sample filter assembly, or another spectral line of the non-target species where absorption or emission by that non-target species is the same as or comparable in magnitude to the absorption or emission by that non-target species at the sample spectral line. Using such a configuration, the output of the detector output comparison device will be indicative of the net target species absorption or emission corrected for the effects of the selected background species such as an atmospheric gas or gases.

In another embodiment of the remote sensor of the present invention, a sample filter assembly is positioned in the first optical path, the sample filter assembly including a notch filter (a filter which blocks one frequency or a range of frequencies but transmits the rest of the spectrum). The sample notch filter may be configured to attenuate at a frequency that coincides with a selected spectral line of a target species, and the second optical path may include no filter at all and therefore provide no attenuation. Alternatively, accuracy may be improved by positioning a blank in the second optical path, the blank being made of the substrate of the sample notch filter. In addition, a bandpass filter with a frequency center that coincides with the sample notch filter may be placed either in front of both the first and second optical paths before the sample notch filter and blank, or after both the sample notch filter and blank.

The sample and reference filter assemblies may be made up of several paired sets of sample and reference filters. The sample and reference filters may include one or more striped filters having a repeating sequence of a plurality of filters for simultaneous detecting a plurality of target species. The use of striped filters provides a scalable imaging capability to the present remote sensor. Where a plurality of filter pairs are used, a corresponding plurality of detectors or detector arrays may be used.

The detector output comparison device may be configured to minimize or eliminate common background noise components, differences in light or other radiation source power, and absorption or emission by interfering species. The detector output comparison device may include a computer, lock-in amplifier or other suitable devices, or a combination thereof, for subtracting and/or normalizing the sample and reference signals. Where applicable, it preferably includes noise cancellation circuitry, such as one or more balanced ratiometric detector (BRD) assemblies, for this purpose.

In embodiments where the remote sensor of the present invention employs a single detector assembly for both the first and second optical paths, the sensor may include a first beam splitter configured to transmit a first portion of the light or other radiation along the first optical path and to reflect a second portion of the light or other radiation along a second optical path. In such a configuration, the sample filter assembly is positioned in the first optical path after the first beam splitter, and the reference filter assembly is positioned in the second optical path after the first beam splitter. A single detector assembly is positioned after the sample and reference filter assemblies, and means for directing the first and second portions of the light or other radiation to the detector assembly is positioned between the sample and reference filter assemblies and the detector assembly. The directing means may include mirrors for altering the direction for the first and second portions of the light or other radiation, as required, and/or a second beam splitter. In addition to, or instead of, the mirrors and second beam splitter, the directing means may include a switching device which alternately permits the first portion of the light or other radiation to reach the detector assembly while preventing the second portion from doing so, then permits the second portion of the light or other radiation to reach the detector assembly while preventing the first portion from doing so. When such a directing means is used, the detector output comparison device may include a memory device and/or a computer or other data processing device to store the first output of the detector assembly produced when the switching device directs the first portion of the light or other radiation to the detector assembly, so that such first output may be compared to the subsequent second output. The switching device may be any suitable device, and preferably comprises a simple and rugged mechanical shutter device or slotted chopper wheel device.

The sensor of the present invention preferably will include light collecting optics, sample and reference filter assemblies, one or more detector assemblies and detector output comparison devices configured such that the sensor may be used as a remote sensor. The sensor may be made in any form for such use, such as in a camera-shaped, gun-shaped, headset or binocular configuration (e.g., with one "eye" containing the sensor and the other "eye" containing a visual telescope) for handheld use, in a configuration useful for positioning on the ground or in the ocean, or in a configuration useful for mounting in an aircraft. Preferably, the sensor is configured to operate on a low power DC power supply such as a 12 V battery.

The present invention also includes a method of determining the presence, concentration and/or optical density of a target species. The method generally includes the steps of receiving light or other radiation that has been absorbed by or emitted from a target species; directing the light or other radiation along two optical paths, one passing through a sample filter assembly and the other through a reference filter assembly, or, optionally, a filter blank or no filter at all; directing the light or other radiation along the first path from the sample filter assembly to a detector assembly and detecting its power using the detector assembly; directing the light or other radiation along the first path from the reference filter assembly to the detector assembly and detecting its power using the detector assembly; and using a detector output comparison device, such as one or more BRDs, to compare the sample signal to the reference signal and produce a signal which is indicative of the absorption or emission of the light or other radiation by the target species.

The method may include, if it is desired to use a single beam of light or other radiation for detection, receiving such a beam of light or other radiation that has been absorbed by or emitted from a target species; splitting the light or other radiation into a first portion and a second portion; directing the first portion along a first optical path and through a sample filter assembly, and directing the second portion along a second optical path and through a reference filter assembly; directing the first and second portions from the sample filter assembly to a detector assembly; detecting the power of the first and second portions of the filtered light or other radiation using the detector assembly; and using a detector output comparison device to compare the sample signal to the reference signal and produce a signal which is indicative of the absorption or emission of the light or other radiation by the target species. The method of the present invention may be performed using the remote sensor of the present invention, or various components of such a remote sensor.

It will be appreciated that, although the present invention is discussed in terms of what is perhaps its most useful application, the detection of gases, it may be employed to detect and evaluate not only gases, but liquids, solids, chemicals adsorbed to interfaces, plasmas, and combinations thereof.

Accordingly, it will be appreciated that the remote sensor and chemical sensing method of the present invention may be used to remotely detect and determine the presence, concentration and optical density of any gaseous agents of interest, such as dust, $CO_2$, $O_3$, $CH_4$, propane, $N_2O$, $NO_x$, CO, hydrogen and hydrocarbon fires, and liquid spills and plasmas.

The foregoing and other features, objects and advantages of the present invention will be apparent from the following detailed description, taken in connection with the accompanying figures, the scope of the invention being set forth in the appended claims.

BRIEF DESCRIPTION OF THE DRAWINGS

The accompanying drawings, which are incorporated into and form a part of the instant specification, illustrate several aspects and embodiments of the present invention and, together with the description herein, serve to explain the principles of the invention. The drawings are provided only for the purpose of illustrating preferred embodiments of the invention and are not to be construed as limiting the invention. In the drawings.

DETAILED DESCRIPTION OF THE INVENTION

Figure 1:
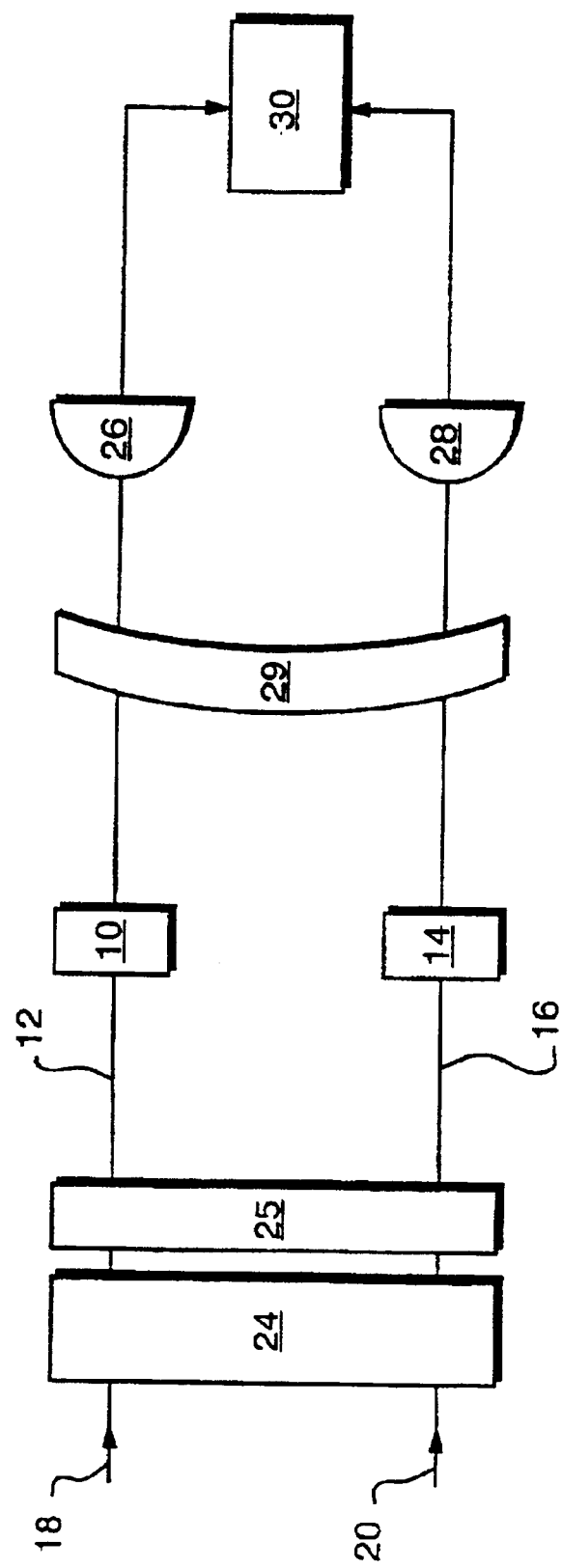
FIG. 1 is a schematic illustration of one embodiment of the sensor of the present invention.

As illustrated schematically in FIG. 1, the sensor of the present invention generally comprises a first filter assembly 10 positioned in a first optical path 12, and a second filter assembly 14 positioned in a second optical path 16. First and second optical paths 12 and 16 may correspond to wholly separate first and second beams of incident light 18 and 20, as shown in FIG. 1, or may correspond to beams derived from a single incident light beam 22, as illustrated in connection with the embodiments of FIG. 2. The term "light," as used throughout the present application, is intended to include any wavelength of optical radiation, regardless of source, from the ultraviolet (UV) through the infrared (IR) regions of the spectrum.

The incident light beam to be detected typically is the product of the absorption or emission spectra by a target chemical species. For absorption, radiation from artificial sources such as lamps, lasers, glow bars, light emitting diodes, or black body sources, or natural sources such as the sun, or far infrared sources such as the ground, buildings or living beings passes through the target species. Emission spectra are obtained when the target species is warmer than its surroundings, e.g., when detecting a cloud of chemical pollutants by a far infrared detector facing the sky. The incident light or radiation beam(s) are formed by radiation emitted by a target species or passing through a target species from a natural or artificial light source.

In the dual-beam embodiment of FIG. 1, first filter assembly 10 may be referred to as "sample" filter assembly 10, and second filter assembly 14 may be referred to as "reference" filter assembly 14. First incident light or radiation beam 18 and second incident light or radiation beam 20 are collected by suitable light collecting optics 24, which may comprise one or more optical elements known to the art including, for example, lenses, holographic lenses, mirrors, optical fibers, optical filters, slits, apertures or the like. Once first and second incident beams 18 and 20 have been collected by light collecting optics 24, light is passed through sample filter assemblies 10 and 14. As discussed in detail below, sample and reference filter assemblies 10 and 14 may be bandpass or notch filters. Where they are notch filters (or when sample filter assembly 10 is a notch filter and reference filter assembly 14 is not included, as will be described), an additional bandpass filter assembly 25, which may include one or more bandpass filters, is positioned in first and second optical paths 12 and 16 to reduce the background radiation passed by sample and reference filter assemblies 10 and 14. Bandpass filter assembly 25 may be positioned anywhere in first and second optical paths 12 and 16, and preferably has a line center at or near the center of the sample filter, as well as a slightly larger bandwidth.

The power of the light or radiation is detected by sample and reference detector assemblies 26 and 28, respectively. Sample and reference detector assemblies 26 and 28 produce sample and reference signals, respectively, which are indicative of the power of incident beams 18 and 20 passing through sample filter assemblies 10 and 14. The detection of second incident light or radiation beam 20 preferably is accomplished simultaneously with the detection of first incident light or radiation beam 18, as simultaneous detection of the sample and reference signals may provide a more realistic background subtraction and higher detection sensitivity. The detectors used in connection with the present invention, including sample detector assembly 26 and reference detector assembly 28, may include any detector known to the art, such as, for example, an infrared detector or infrared focal plane array (FPA), photo-diode, avalanche-photo-diode, photomultiplier tube, semiconductor detector (e.g., including silicon, germanium, gallium arsenide, indium arsenide, indium gallium arsenide, indium antimonide, lead sulfide, lead selenide, mercury cadmium telluride), thermal detector (e.g., pyroelectric, thermopile or bolometer), charge-coupled device, linear-diode array, or linear-detector array.

The outputs of the sample and reference detectors are compared to each other by a detector output comparison device 30, the output of which may be displayed or conveyed to a user in any convenient manner. For example, the output may be electronically formed into a video image. Detector output comparison device 30 may include a computer, lock-in amplifier or another similar device to subtract the sample detector signal from the reference detector signal, or vice-versa. Detector output comparison device 30 may also, or alternatively, include noise cancellation circuitry, such as a balanced ratiometric detector (BRD) or another system which is capable of providing high quality signal, to divide the difference between the sample and reference detector outputs by either the sample or reference detector signal. A BRD assembly is capable of performing the subtraction function, then dividing the difference of the sample and reference signals by the signal measured either by detector assembly 26 or 28 to provide a normalized difference (e.g., (A-B)/B, (B-A)/B, (A-B)/A, or (B-A)/A, where A is the reference detector signal and B is the sample detector signal). Of course, it will be appreciated that a digital computer or lock-in amplifier, as well as other conventional devices, could be used to perform some or all of the functions of a BRD. Comparing the sample and reference signals effects the elimination or reduction of common noise components, variations in source power, and absorption by interfering species (where bandpass filters are used), such that only the net target species absorption or emission is recorded. Normalizing the signals further permits the positive identification of the target species signature while rejecting the signatures of other species. Thus, a unique feature of this technique is that a rather complex spectral analysis is reduced to a simple differential measurement, and, optionally, normalization.

Figure 2:
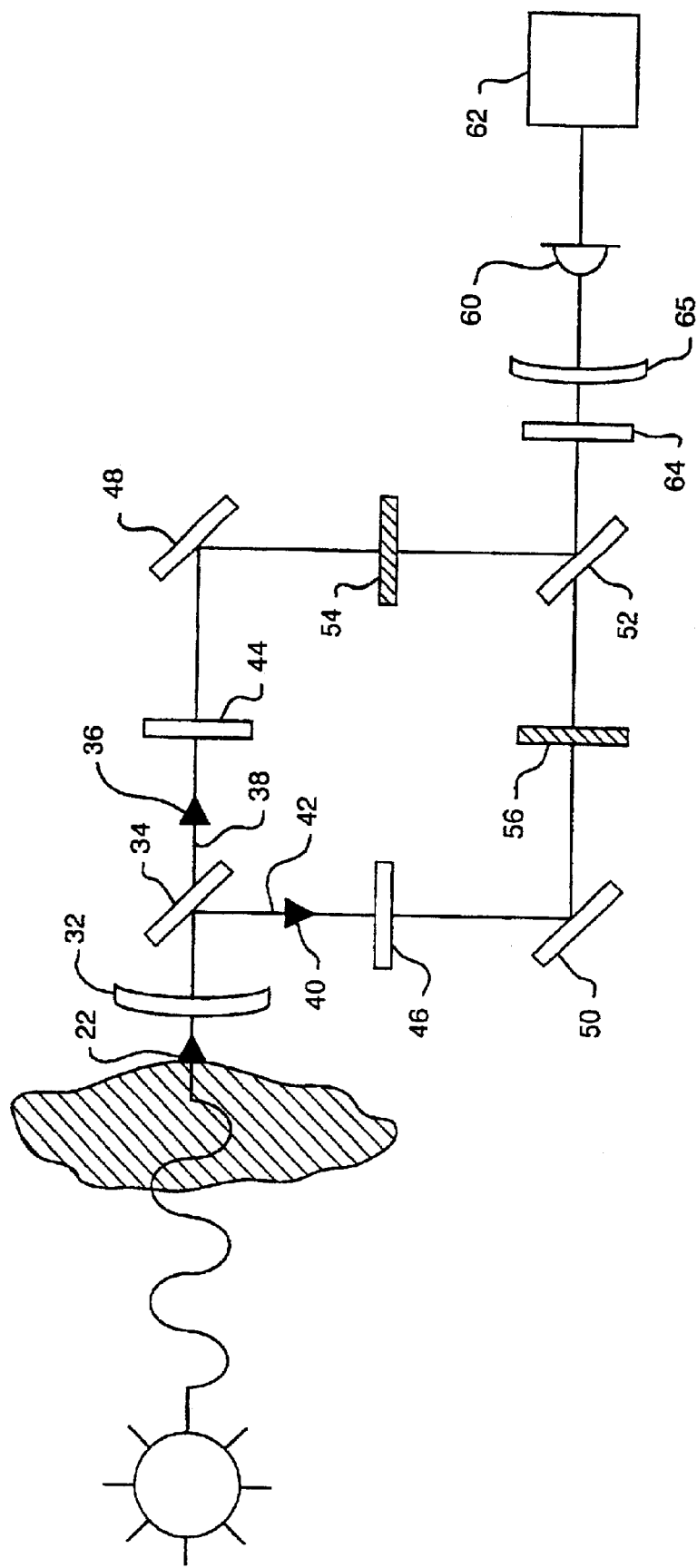
FIG. 2 is a schematic illustration of another embodiment of the sensor of the present invention.

In contrast to a dual incident light or radiation beam configuration of the sensor of FIG. 1, the single beam configuration illustrated in FIG. 2 makes possible the use of a single detector, which is beneficial because it allows comparing two images, one obtained through the sample filter assembly and one through the reference filter assembly without loss of registration. It also reduces cost when an expensive detector such as a FPA is used. Finally, it can improve accuracy and sensitivity when the gains of the two detectors of FIG. 1 cannot be matched to each other.

In the embodiment of FIG. 2, single incident light or radiation beam 22 is collected by light collecting optics 32 and divided by a first beam splitter 34 into a first portion 36 of incident beam 22 transmitted along a first optical path 38 and a second portion 40 of beam 22 reflected along a second optical path 42. First and second light or radiation beam portions 36 and 40 then are passed through a first filter assembly 44 (which may be referred to as a "sample" filter assembly 44) and second filter 46 (which may be referred to as a "reference" filter 46), respectively. Like sample and reference filter assemblies 10 and 14 in FIG. 1, sample and reference filter assemblies 44 and 46 may be bandpass or notch filters, as is discussed in detail below. First and second beam portions 36 and 40 then are redirected by a first mirror 48 and a second mirror 50, respectively, and a second beam splitter 52 preferably is employed to recombine first and second portions 36 and 40 of light or radiation beam 22 after they pass through sample and reference filters 44 and 46. First and second switching devices 54 and 56 are used to modulate or selectively direct first and second portions 36 and 40 of beam 22 to a detector 60, and may be positioned anywhere between light collecting optics 32 and detector 60. First and second switching devices 54 and 56 may be separate devices, or may be a single device such as a chopping wheel or tunning fork chopper.

Accordingly, in the embodiment of FIG. 2, a single detector assembly 60 alternately receives the signals from first optical path 38 and second optical path 40. For example, detector assembly 60 may first detect the power of first portion 36 of beam 22. The detector assembly 60 produces a sample signal based on this detection, and the sample signal is stored in a memory device, which may be part of a detector output comparison device 62, such as a conventional computer memory. Then switching devices 54 and 56 operate to direct second portion 40 of light or radiation beam 22 to detector assembly 60, which will produce a reference signal indicative of the power of second portion 40 of beam 22. Detector output comparison device 62 may further include a computer, lock-in amplifier or another such signal processing device from the art of synchronous detection and signal processing (not shown), which may then be used to subtract the reference signal from the sample signal. Detector output comparison device 62 also preferably includes a device which normalizes the resulting difference in a manner described in connection with detector output comparison device 30 in the embodiment of FIG. 1. The normalization device may be a digital computer (which may store the sample and reference signals, subtract them, and normalize them), a lock-in amplifier or another device capable of performing the normalization function.

The net target species absorption or emission may then be recorded. As previously discussed with respect to bandpass filter assembly 25 of FIG. 1, a bandpass filter assembly 25 (FIG. 1) or 64 (FIG. 2) optionally may be positioned before detector assemblies 26 and 28 (FIG. 1) or detector assembly 60 (FIG. 2) to further reduce unwanted radiation outside the detection bandwidth. In FIGS. 1 and 2, light collecting optics 24 and 32 are used to collect and collimate the light or radiation in optical paths 12, 16 or 38, 40. A lens assembly 29 (FIG. 1) and 65 (FIG. 2) is used to focus the radiation on detector assemblies 26 and 28 in FIG. 1, and detector assembly 60 in FIG. 2.

Operation of the BRD

The use of a BRD assembly (or an equivalent device as previously discussed) in detector output comparison device 30 (FIG. 1), in connection with the sensor of the present invention, makes possible the subtraction of the common noise-components of the reference detector assembly from that of the sample detector assembly (or vice-versa) at an accuracy level that approaches the shot-noise limit. This assembly also effects the normalization of the detected signal by dividing the difference by either the sample detector signal or the reference detector signal. It will be appreciated that there are several noise components that can limit optical measurements, but the fundamental limitation to all measurements is the statistical (or shot) noise that results from the discrete nature of photons and electrons. Shot-noise can be reduced only by increasing the optical signals (with the exception of large background signals, which contribute to the shot noise but do not have meaningful content) or by using a long integration time. Therefore, after selecting certain design parameters the level of shot noise can no longer be controlled. A design objective of all instruments therefore is to eliminate excess noise, i.e., noise components above and beyond the shot noise. Excess noise may result from variations in the background radiation, such as variations in the brightness of the sky, electromagnetic noise, and drifts in detector response such as those due to slow changes in its temperature, among other factors. Few techniques are available to correct for excess noise that is common to all the detectors used, where a sensor system having more than one detector is employed. Some rely on dividing the signal obtained by one detector by the signal of the other, although such dividers tend to be noisy and are difficult to use during setup of the optical system because of the need for a denominator voltage. One of the best dividers currently available has characteristics that are about 60 dB worse than the best op-amp.

Subtraction is another alternative for the removal of common components of excess noise. Typically, it is achieved by feeding the photocurrents of both sample and reference detectors to the summing junction of an operational amplifier (op-amp) and recording its output. Unfortunately, large variations in the DC level of the signal can satuate the amplifier, preventing the resolution of small signals. For detection in the long-wave infrared (8–13.3 $\mu$m), such large DC levels may be induced by the thermal emission of uncooled optical filters themselves. Thus, to use uncooled optical elements or detectors, which is preferable for some applications such as handheld or unattended sensors, subtraction of the signal induced by their thermal emission must take place before the signal is amplified to avoid reduction in the dynamic range. Several approaches may be used for such pre-amplified subtraction, but the BRD is superior in that it is very accurate, compact, fast, inexpensive, and integrates the normalization of the sample and reference signals. In addition, the BRD has had demonstrated success in other fields of use.

The BRD may be of the type described in U.S. Pat. No. 5,134,276, issued Jul. 28, 1992 to Hobbs, which is incorporated by reference herein in its entirety. It is a commercially available, simple electronic circuit designed to overcome the deficiencies of both the direct subtraction and direct division techniques. For example, a BRD may be purchased from New Focus (Santa Clara, Calif.). The BRD reduces excess noise by monitoring the signals of the sample and reference detectors simultaneously and creating an electronic photocurrent balance between the two. Although the technique was developed for optical communication, Sonnenfroh, et al. have found that, for example, direct absorption measurements of $NO_2$ using a BRD yield detection sensitivities of one part in $10^{-6}$. See Sonnenfroh, et al., "Ultrasensitive, Visible Tunable Diode Laser Detection of $NO_2$," App. Opt., vol. 35, at 4053–58 (1996). For BRD measurements in connection with systems such as that shown in FIG. 1, one detector views the signal through sample filter assembly 10, which includes some background radiation, and provides the sample photocurrent $I_S$. The reference detector assembly 28 views the target species through reference filter assembly 14, and provides the reference photocurrent $I_R$ that corresponds just to background radiation. Cancellation of excess noise by more than 50 dB and of large common DC components is achieved by balancing the photocurrents of each of the detectors just before the op-amp. Thus the amplified difference at the output of the op-amp is near zero. Effectively, the circuit attempts to continuously maintain a preset ratio between $I_S$ and $I_R$ using a negative feedback that holds the output of the op-amp near zero. Typically, the sample current is set to be $I_S > I_R$. When the currents of both detectors change simultaneously, there is no observable change in the current of the feedback line. However, when the current of only one of the detectors, i.e., the sample detector, changes because a detectable absorption by a target species, the feedback line attempts to rebalance the currents to their preset ratio. The voltage in the feedback line is:

$$V_o = -\ln\left(\frac{I_S - I_R}{I_R}\right)$$

Thus, measurement of the feedback voltage can be used to directly measure the difference between the sample and reference currents normalized by the reference current. This single step subtraction and normalization is attractive because dependence of the measurement on the absolute value of the radiation as well as the excess noise modulation is removed. Furthermore, because the input to the op-amp is reduced to $I_S - I_R$, large DC components such as thermal emission by the bandpass filters themselves are eliminated before amplification, thereby allowing high gain detection without saturating the amplifier. This unique feature together with the large detection bandwidth permits measurement of low signals even when the background level is high, such as in the use of uncooled detectors and uncooled filters in the far infrared for remote sensing, while providing high sensitivity. Given the low-cost and small size of all the components, simultaneous detection of several target species, or improved specificity by the detection of additional spectral lines of the same species, may be possible by combining several pairs of sensor assemblies (e.g., in the configuration of FIG. 1) with a detector output comparison device having multiple BRD circuits, one BRD circuit for each pair of sensor assemblies.

Selection of Filters

In the embodiments of FIGS. 1 and 2 of the present invention, species-specific detection may be accomplished by selecting as sample filter assembly 10 or 44 a bandpass filter that transmits within a narrow band (e.g., in the far infrared 15 cm$^{-1}$) centered at a frequency that coincides with an absorption or emission line of one or more target species, and selecting as reference filter assembly 14 or 46 a bandpass filter having the same or approximately the same bandwidth but a center frequency that does not coincide with any prominent absorption or emission line of the target species. Instead, the center frequency of reference filter assembly 14 or 46 may be selected to coincide with one or more of the spectral lines of prevalent or influential background, or non-target, species such as one or more atmospheric gases (for example, one or more of $H_2O$, $CO_2$ or $O_3$), such that the transmission by the reference filter assembly 14 or 46 of the absorption or emission of the selected atmospheric gas or gases or other non-target species is the same magnitude as, or comparable in magnitude to, the transmission by the sample filter assembly 10 or 44 of the absorption or emission of the same species. More advantageously still, a second sample filter assembly may be used that coincides with another absorption (or emission) line of the same target species, and a reference filter assembly that corrects for the absorption (or emission) by non-target species that coincide with the transmission band of the second sample filter assembly. Using two different pairs of filter assemblies for the detection of two separate spectral lines of the same target species provides additional means for identifying that target species, even in the presence of spectroscopically similar, non-target species. Similarly, additional filter assembly pairs can be added for detection of other target species and correction of background signals associated with them.

Such a filter selection forms a new type of Differential Absorption Radiometer (DAR). The effect of the DAR design of the present invention is that interference by the selected non-target species on the sample detector assembly 26 or 60 may be eliminated or minimized, effecting an increase in the sensitivity and specificity of detection of the target species.

The combination of the DAR and the BRD assembly in accordance with the present invention is particularly attractive for handheld or unattended target species detection (for example, on remotely piloted vehicles), because such a system (1) may be used for target species detection regardless of atmospheric conditions (e.g., humidity, rain) and against various backgrounds (such as buildings, topography, or cloudy skies), (2) allows positive identification of one or more target species even in the presence of other species that are spectroscopically similar, (3) permits easy interpretation of its results by untrained operators, without complex in-field computations, (4) makes possible the use of broadband detection and high throughput that results in low noise equivalent spectral radiance (NESR), even, for example, with uncooled far-infrared detectors, (5) when configured for single point measurement, utilizes a unique subtraction technique that provides shot-noise limit detection and prevents saturation of pre-amplifiers used in the system even, for example, in the presence of large emission by uncooled far-infrared optical components, (6) is compact, energy efficient, light and robust, as is necessary for systems intended to be used as handheld or unattended sensors, and (7) can be configured with large FOV consistent with requirements for imaging.

Alternatively, even greater sensitivity may be possible using an alternative embodiment of the sensor of FIGS. 1 or 2 wherein sample filter assembly 10 or 44 comprises a notch filter with an attenuation band that coincides with a prominent spectral feature of the target species, and reference filter assembly 14 or 46 comprises a blank made of the substrate of the notch filter of sample filter assembly 10 or 44. Detection also may be accomplished at a reduced sensitivity even without the blank in the reference path. Radiation collected by light collecting optics 24 or 32 and passed through bandpass filter 25 or 64 is passed once through the notch filter and then through the reference blank (or along the reference path without a reference filter blank). As with the DAR system, it is then recorded simultaneously by detectors 26 or 28 (FIG. 1), or alternatively for each path by detector 60 (FIG. 2). Such a filter selection forms a type of Notch Filter Correlation Radiometer (NFCR), which is capable of distinguishing between absorption or emission by a target species and interfering background radiation by correlating that spectral feature with the notch filter line. When a target is viewed through the reference blank 14 or 46, all its radiation within the limited system bandwidth, defined by bandpass filter assembly 25 or 64, is transmitted with nearly no attenuation. Therefore, it includes large background components such as albedo for atmospheric sensing or thermal emission by objects in the field of view (FOV) for infrared sensing, combined with the absorption (emission) by the target species. Often the contribution by the target species is too small to be detected directly. But when the target area is viewed through a notch filter assembly 10 or 44 that has a band that matches a prominent spectral feature of the target species, that specific feature is selectively attenuated. The background itself, which may include spectral lines of other species that do not match the attenuation spectrum of notch filter assembly 10 or 44, is only slightly attenuated. Therefore, subtracting the signal obtained through the reference blank 14 or 46 from that obtained through the notch filter assembly 10 or 44 cancels most of the interfering features that were outside the notch filter band and part of the features that coincide with that band. This difference is strongly related to the correlation (or match) between the band of the notch filter assembly 10 or 44 and the spectrum of the target species and can be used to positively identify the target species signature and measure its optical density C×L (where C is concentration and L is optical path) while rejecting interference by the background or other agents. As shown in FIGS. 1 and 2, to further reduce interferences by radiation or unrelated spectral features, the detection bandwidth may be limited by a bandpass filter assembly 25, or 64, that may be positioned somewhere between light collecting optics 24 or 32 and detectors 26 and 28 or detector 60, along a path common to the sample and reference paths. Bandpass filter assembly 25 or 64 is chosen to pass at a range of frequencies where the signature of the target species is most pronounced (e.g., to an approximately about 15 $cm^{-1}$ range around 1086 $cm^-$for the detection of DMMP).

The NFCR may be used for remote sensing or remote imaging. For example, for imaging, where a chemical cloud in the atmosphere is to be detected using the NFCR system and a single IR FPA as detector 60, the image obtained through reference blank 46 may be stored digitally and then subtracted pixel-by-pixel from the image obtained separately through notch filter assembly 44. The difference between these two images may not vanish even in the absence of the target species. However, with an atmospheric effluent or other target species in the FOV, that difference varies relative to the surroundings, thereby providing an image of the distribution of the target species. Of course, the magnitude of this difference depends upon, among other things, the overall magnitude of the incident radiation, which in turn depends on parameters, such as albedo or surface temperature in the case of sensing infrared radiation, that vary from point to point or from pixel to pixel on the FPA. To correct for such variations, the difference image may be normalized by a BRD assembly or other such system, when using an NFCR such as that illustrated in FIG. 1 for point measurements, or simply by dividing the difference pixel-by-pixel with the image obtained through the reference blank, as may be the case when imaging. The NFCR system is particularly useful for imaging and detection from fast moving platforms where the speed of data processing must match the high imaging rate. The NFCR system is well-suited for broad area search, acquisition and targeting of fixed or mobile agents, having the same advantages as previously discussed in connection with the combination of the DAR and the BRD assembly.

Both the NFCR and the DAR may be considered multispectial or simplified hyperspectral imaging techniques. In most hyperspectral techniques that are presently proposed, an entire spectrum is scanned rapidly by a dispersive or interferometric imaging spectrometer and numerous images of the target are recorded, each at a specified wavelength and bandwidth. See, e.g., Gittins, et al., "Passive Standoff Infrared Detection of Bio-Aerosols," $4^{th}$ Joint Workshop on Standoff Detection for Chemical and Biological Defense, Williamsburg, Va., Oct. 26–30, 1998; and Hinnrichs, et al., "Remote Sensing for Gas Plume Monitoring Using State-of the Art sired Hyperspectral Imaging," $4^{th}$ Joint Workshop on Standoff Detection for Chemical and Biological Defense, Williamsburg, Va., (Oct. 26–30, 1998). Thus, when sensing in the far-infrared, approximately 40 images, each recorded at a bandwidth of 10 $cm^{-1}$, are needed to cover an 8–13.3 $\mu m$ range. When combined with the need for high spatial resolution (i.e., large number of pixels), the demand for digital storage and processing becomes significant. Perhaps even more importantly, available FPAs provide imaging rates of less hand 50 Hz. Thus, recording a full hyperspectral scan takes nearly one second. From a moving platform, the image at the start of such scan may not contain the same ground features as the image at the end of the scan, thereby complicating or even preventing accurate point-by point spectral processing. By contrast, both the NFCR and the DAR embodiments of the present invention require only two images that can be recorded within 1/25 sec. At 500 miles/hr, as may be the case when imaging from an airborne platform, the spatial shift between the two images at that rate will be less than 30 ft and may be corrected by digitally shifting the images before processing.

The NFCR and DAR embodiments of the present invention also provide other important advantages. For example, the DAR can provide superior detection sensitivity from short distances. On the other hand, it is more susceptible than the NFCR to interference by absorption by non-target species or to spectral variations of the albedo for atmospheric remote sensing. Consequently, variations in the detection path (e.g., by motion) or its constituents (e.g., weather for atmospheric sensing) have a larger effect on measurements with the DAR than the NFCR, which inherently corrects for such interfering effects.

Figure 3:
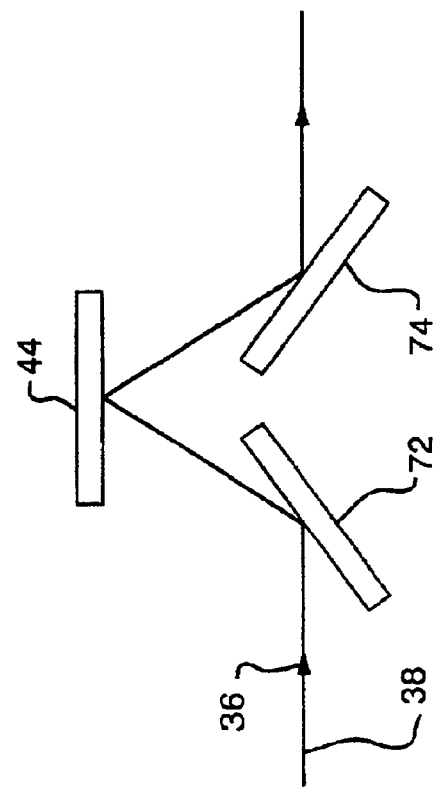
FIG. 3 is a schematic illustration of a technique for using a bandpass filter as a notch filter in the sensor of the present invention.

For use in a DAR type sensor, bandpass filters in the ultraviolet (UV), visible and infrared (180 nm–20 $\mu m$) ranges are available from several manufacturers. Typically, they may be custom designed for specified line-centers, specific bandwidth (e.g., 11 $cm^{-1}$ or 15 $cm^{-1}$ in the far infrared and less than 1 $cm^-$in the visible and UV) and peak transmission (e.g., greater than 0.64). In certain applications, the filters can replace the detectors' windows, thereby providing an integrated design to reduce size while providing mechanical support to the thin filters. For use in the NFCR, notch filters are available in the UV and visible region from several manufacturers and can be attached directly to the detector while replacing its window. Presently, there do not appear to be any notch filters available commercially in the far infrared. However, functionality of a notch filter can be achieved by using the reflection off the surface of a dielectric-coated bandpass filter having the same characteristics as the desired notch filter. This is illustrated in FIG. 3, where first and second mirror 72 and 74 are added to the embodiment of the device shown in FIG. 2 to reflect first portion 36 of beam 22 off the surface of a dielectric-coated bandpass filter 44 and return it to its original path, first optical path 38. A similar notch filter may be configured for use in the embodiment of the present invention illustrated in FIG. 1.

Irrespective of whether a NFCR or DAR type sensor is used, the spectrum of the target species to be identified and the non-target species to be corrected must be analyzed in order to determine the characteristics of bandpass or notch filters to be used in the sensor. This is a result of the fact that remote sensing techniques of toxic agents, atmospheric pollutants and other potential target species necessarily utilize either the emission or absorption properties of such species, such that the radiation between a light source (natural or artificial) and the target species, and then between the target species and the detector, must propagate through the atmosphere and other interfering substances.

The NFCR and DAR may be used for atmospheric remote sensing. In that application, atmospheric transmission is an important parameter. Atmospheric transmission is a complex interplay between molecular absorption and scattering, aerosol absorption and scattering, and atmospheric index of refraction varations. Molecules such as $H_2O$, $CO_2$, $O_3$, $CH_4$ and $N_2O$ mainly cause molecular absorption. Aerosols contribute significantly when their density is high, e.g., clouds and fog (this is in addition to the molecular absorption of their constituents). Turbulence may also affect some measurements. However, it is anticipated that subtraction and normalization by a BRD assembly or other normalization device in accordance with the present invention will correct most effects of aerosols and turbulence and, depending on the selection of the reference filter where bandpass filters are used, also most of the atmospheric molecular absorption. Therefore, as long as the signal induced by the target species itself exceeds all noise sources, detection may be possible, albeit at reduced sensitivity, by either a DAR or NFCR even in the presence of precipitation, clouds or fog.

To avoid excessive attenuation by atmospheric absorption, each DAR or NFCR sensor must operate within a limited atmospheric window. Although the exact extent of these windows depends on the detection range and acceptable attenuation, the most significant windows are believed to be in the wavelength ranges of from about 0.3 μm to about 1.5 μm, from about 3 μm to about 5.5 μm, and from about 8 μm to about 13.3 μm.

For passive detection of target species, the optical absorptions and emissions of such target species must occur by transitions between naturally populated states (unlike LIF where emission is by transitions between artificially excited states). Therefore, passive detection is mostly limited to the infrared and far infrared where vibrational and rotational transitions occur within the ground electronic state (transitions between electronic states mostly occur in the solar blind UV and are typical to hot media such as flames, plasmas and electric discharges). Most toxic chemicals have strong absorption features in the 3.3–4.2 μm and 8–13.3 μm ranges, which also fall within two of the previously mentioned atmospheric windows. However, the bands of many relevant target species in the 3.3–4.2 μm range also coincide with strong C—H stretches in the 3.1–4.1 μm range by many atmospheric hydrocarbons which may interfere with positive identification. Thus, the 8–13.3 μm range appears to be the most suitable for passive remote atmospheric sensing.

Figure 4:
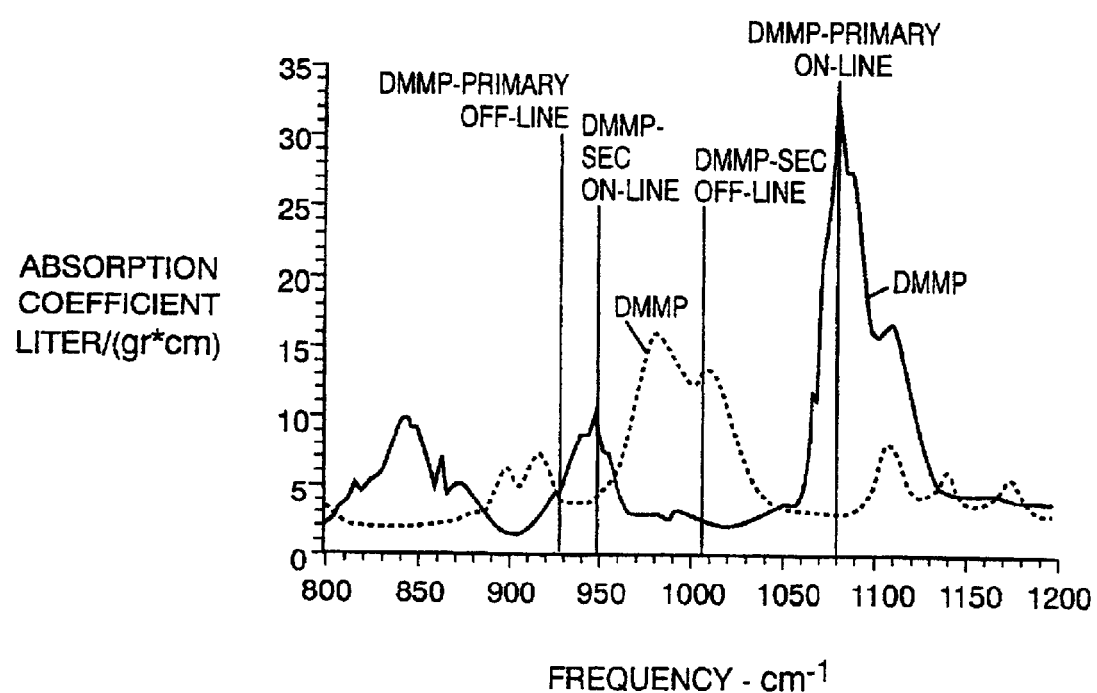
FIG. 4 is a graph illustrating the absorption coefficient/frequency curves for DIMP and DMMP, and exemplary sample and reference filter selections for two DMMP-DAR sensors.

FIG. 4 illustrates, as an example, the spectral variation of two agents that are used as pesticides, dimethyl methylphosphonate (DMMP) and diisopropyl methylphosphonate (DIMP). Since both have spectral features that are similar to those of other highly toxic chemicals, including band-peak frequency, bandwidth and absorption coefficients, they are often used as spectroscopic simulants in testing remote sensors in the far infrared. Consequently, available reports often describe measurements using DMMP and DIMP as the target species. Aspects of the present invention were also modeled and evaluated using these agents. The spectra shown in FIG. 4 are comparable to those illustrated in Hoffland, et al., *Spectral Signatures of Chemical Agents and Simulants*, Opt. Eng., vol. 24, 982–84 (1985). It is evident that (a) both chemicals have spectral lines that overlap each other at least partially. For example, the primary line of DMMP which is peaked at 1086 cm$^{-1}$ overlaps one of the secondary lines of DIMP, (b) there is no fine structure in their spectra as is normally noticed in the spectra of lighter molecules such $CO_2$, and (c) the absorption coefficients of these lines are exceptionally high. For example the transmission by 0.01 gr*cm/liter (or 16.6 ppm-m at standard atmospheric conditions) of DMMP is 0.72 and by similar optical density of DIMP it is 0.85. These strong absorptions and the lack of fine structure permit sensitive detection of these and similar toxic chemicals even by simple detectors such as the DAR or NFCR of the present invention. On the other hand, the overlap between the broadband lines of two or more species and the lack of fine structure may prevent distinction between spectrally similar species by a single pair of detection paths in the DAR or NFCR sensor configuration. Employing one or more additional detectors pairs (as in FIG. 1) or detection paths (as in FIG. 2) combined with bandpass filters for DAR or notch filters for NFCR configurations may be desirable when distinction between species, i.e., specificity, is required. This is illustrated by the following analysis.

Figure 5:
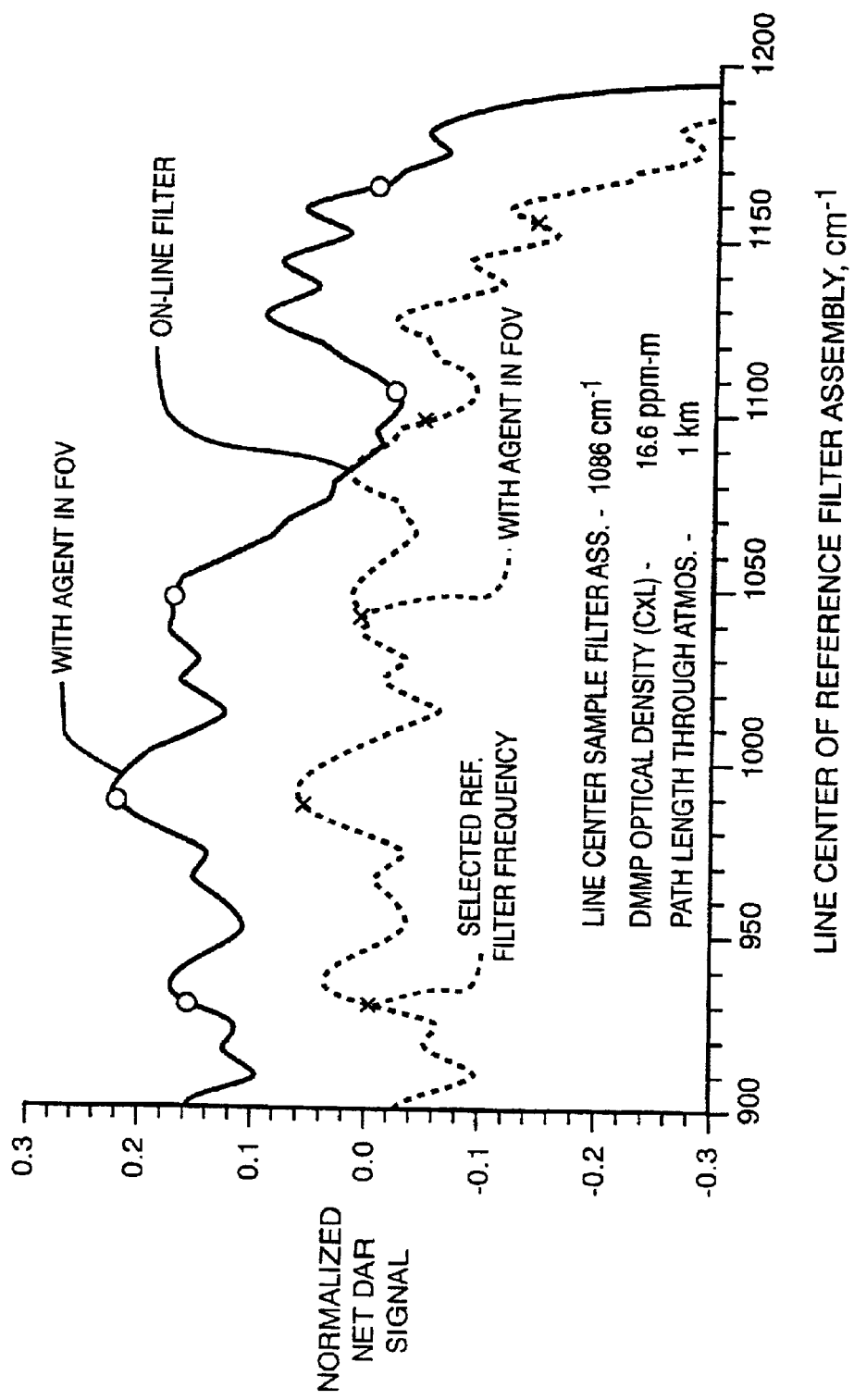
FIG. 5 is a graph illustrating, with DMMP as the target species, the variation of the normalized net DAR signal with reference bandpass filter assembly center-line frequency in a "water only" atmosphere when the radiation source is at 1 km.

A numerical model describing the transmission through horizontal atmospheric paths and by certain target species or agents at various optical densities C×L) was developed in connection with the present invention. The model was used to optimize parameters of the DAR and NFCR when used to detect such species and to estimate the difference between its signal with and without an agent in the FOV. As illustrated in FIG. 5, the variation of the normalized net DAR signal as the center frequency of the reference filter is varied was calculated, assuming an atmosphere containing only water vapor at a partial pressure of 0.00775 atm which is consistent with water concentration in a standard atmosphere, to identify a frequency for the reference filter that optimizes the detection of an agent by the DAR. Although other absorbers such as $CO_{2\ or\ O_3}$ also contributed to this structure, their effect at standard atmospheric conditions is small at 1–3 km from the target and is often predictable at longer distances. This model allowed the selection of a reference filter with which absorption (emission) by water can be optimally corrected. FIG. 5 includes two curves, an upper curve which shows the net normalized absorption signal with C×L=16.6 ppm-m of DMMP (0.01 gr*cm/liter at 297 K and 1 atm) in the FOV, and a lower curve which shows the net absorption signal without that agent. For both of these curves, the center line frequency of the sample filter was at 1086 cm$^{-1}$, where DMMP has a strong absorption. The bandwidth and transmission of both filters were 12.6 cm$^{-1}$ and 0.64 respectively. The normalization was modeled by dividing the photocurrent of each detector with the current of the reference detector, as previously discussed in connection with the BRD assembly. The difference between the absorption measurements with and without species in the FOV varies with the reference filter frequency but it is greater than 15% of the normalizing signal when the reference filter is at 928.5 cm$^{-1}$ and when the IR source is much hotter than the species. This difference is significantly larger than the expected SNR. When the source (e.g., ground) is only 5 K hotter than the species that difference reduces to approximately 1.5%. Similar variations (but with reversed sign) can be expected when the detection of a target species is by emission, i.e., when the target species is warmer then its background.

Figure 6:
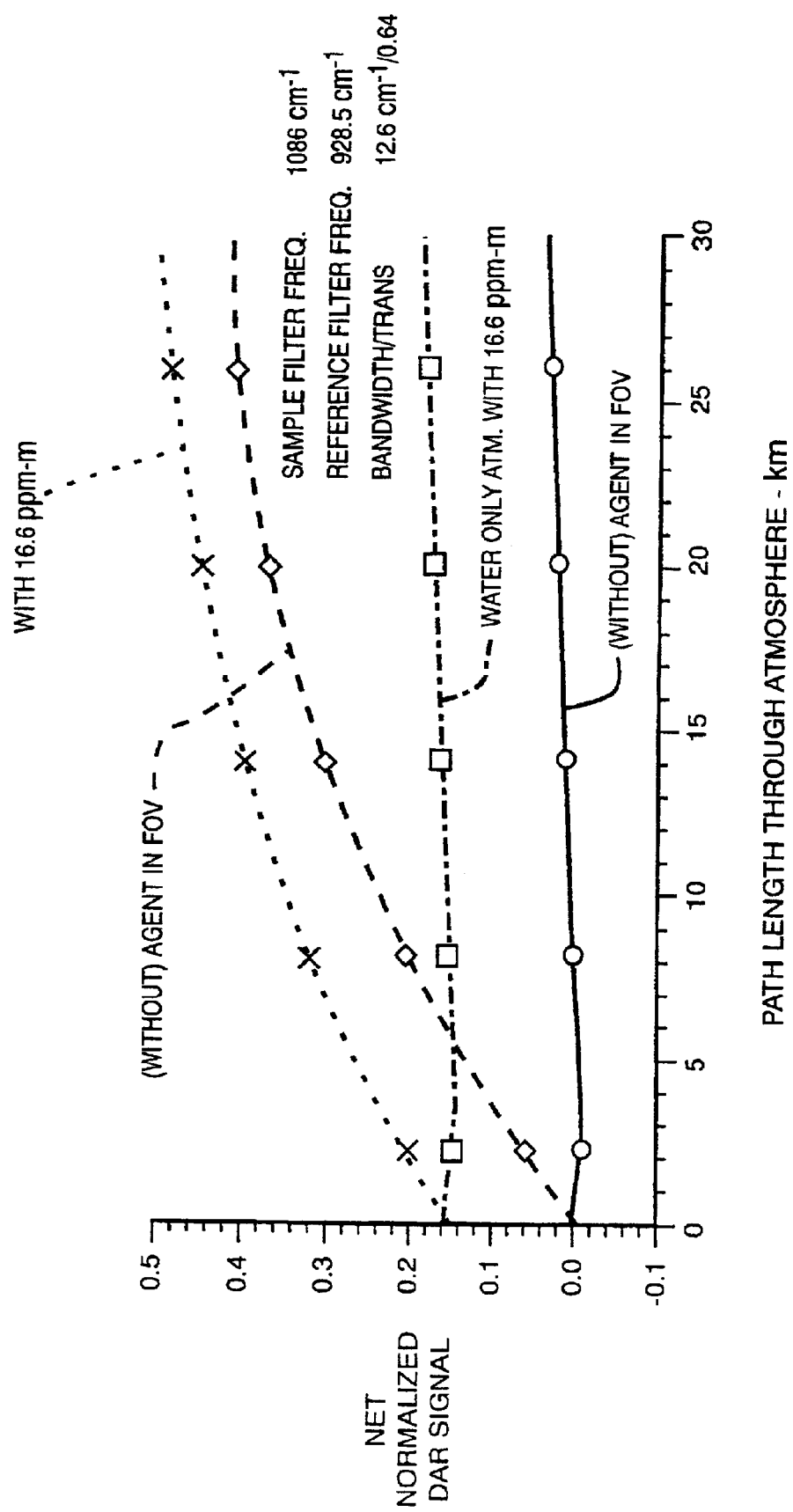
FIG. 6 is a graph illustrating, with DMMP as the target species, the variation of the normalized net DAR signal with path length through "water only" and regular atmospheres.

The results of FIG. 5 also show that when selecting a reference filter with a line center at 928.5 cm$^{-1}$(marked by a vertical line in FIG. 5), the lower curve goes through zero. Thus, a reference filter centered at this frequency can provide a near perfect background cancellation for sample filters centered at 1086 cm$^{-1}$. As shown in FIG. 5, other frequencies can also provide near perfect background cancellation, but with this selection a near perfect correction for absorption (emission) effects by water vapor can extend to large distances. This is illustrated in FIG. 6 where the net normalized DAR signal is seen to remain near zero (lower curve) when the atmosphere contains only 0.0075 atm water vapor and when the detected radiation travels a distance of up to 30 km. The system parameters in this simulation were identical to those of FIG. 5. When 16.6 ppm-m of DMMP are added, the signal increases by more than 15%, but it is still independent of distance. When all the components of the atmosphere are included (top two curves), the measurement is no longer independent of distance but it still remains independent of atmospheric humidity. Clearly addition of 16.6 ppm-m of DMMP into the FOV creates a signal that is large than the background signal of an atmospheric layer of up to 5 km. Thus, when radiation is at distances shorter than 5 km, DMMP can be detected by the absolute reading of the DAR. At longer distances, DMMP can be detected by comparing the reading to an independent reading obtained without agent in the FOV. Thus, by selecting this reference filter frequency for background correction, the detection and measurement of DMMP become independent of atmospheric humidity—a significant advantage for field measurements. Similar optimized background subtraction can be developed for other spectral lines of DMMP, other pesticides, atmospheric effluents or any other target species.

As seen above, the use of one pair of detectors together with one sample filter and one optimally selected reference filter can provide sensitive detection of one target species while correcting for absorption or emission effects of one background gas such as water vapor. However, because of the overlap between some spectral lines of certain agents such as DIMP and DMMP (FIG. 4), one species in the FOV can interfere with measurements by a single DAR or NFCR sensor dedicated to the detection of another agent. For example, a DAR sensor configured to detect DMMP by using a sample filter centered at 1086 cm$^{-1}$ may detect absorption by DIMP that is associated with the line at 1110 cm$^{-1}$. Of course, with sufficiently narrow bandwidth, such as 12.6 cm$^{-1}$ that was used to obtain the data of FIGS. 5 and 6, detection of DIMP through that filter is negligible. However, the reference filter at 928.5 cm$^{-1}$ that was selected to optimally match the absorption by water vapor at 1086 cm$^{-1}$ coincides with a tail of the 917 cm$^{-1}$ DIMP line. Consequently, the subtraction and normalization process that produces an increase in the net normalized DAR signal when DMMP is in the FOV (FIG. 6) produces a decrease in the DAR signal when DIMP is present instead. Thus, a mixture of DMMP and DIMP in the FOV may provide an ambiguous DAR measurement, or in some cases no net signal at all. For example, 0.14 gr*cm/liter of DIMP were shown numerically to produce a negative DAR signal that has nearly the same absolute magnitude as the net normalized signal by 0.01 gr*cm/liter of DMMP. Thus, a DAR sensor optimized to detect DMMP alone may provide no net signal when a mixture of these species in these optical densities is in the FOV. Of course, the sample detector is still providing DMMP-dependent output, but this output alone is not background-corrected and is influenced by atmospheric humidity.

Figure 7:
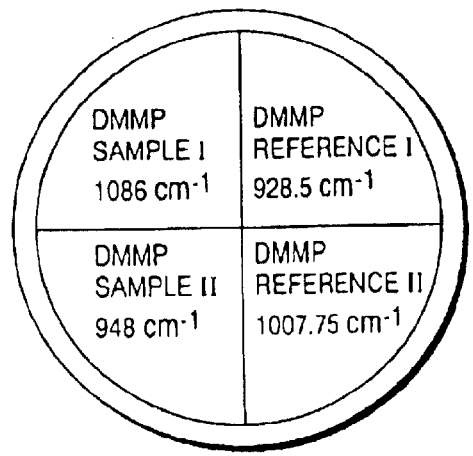
FIG. 7 is a schematic illustration of a quadrant detector which may be used in connection with the sensor of the present invention.

The consequence of his interference by DMMP can be overcome by introducing additional DARs consisting of detector pairs that are either optimized to detect one or more additional lines of DMMP, one or more lines of DIMP, or combinations thereof. For example, a commercially available quadrant detector such as that illustrated in FIG. 7, consisting of four separate detectors, can be configured by the addition of two BRDs to operate as a dual DAR. By attaching bandpass filters at 1086 cm$^{-1}$ and 928.5 cm$^{-1}$ to two of these detectors (e.g., the upper two), they can serve together with one BRD as a primary DMMP DAR sensor optimized for correction of absorption or emission effects by water vapor. A third detector with a bandpass filter centered 948 cm$^{-1}$ to coincide with one of the secondary lines of DMMP and a fourth detector with a bandpass filter centered at 1007.75 cm$^{-1}$ to correct for absorption or emission effects by water vapor together with a second BRD can form a secondary DMMP DAR sensor. In both DARs, the filters are assumed to have a bandwidth of 12.6 cm$^{-1}$ and a peak transmission of 64%.

As shown in Table 1, the net normalized DAR signal measured by the secondary DMMP DAR when 0.01 gr*cm/liter of DMMP is present in the FOV at a distance of 1 km is approximately 4.1% above the background signal. By comparison, the net normalized signal by the primary DMMP DAR (top two quadrant detectors FIG. 7) is 15.5% above the background signal. The ratio between these two signals is comparable to the ratio of the peak absorption coefficients of the corresponding lines of DMMP. Of course, because of the non-linearities associated with strong absorptions by atmospheric molecules and the target species, this ratio may vary as the optical densities of DMMP increase or when the absorption path through the atmosphere increases. Yet, this ratio is preserved to within 25% over a range of 10 km, thereby providing a finger print-like identification of DMMP particularly at short distances and confirming that it alone is present.

Detection by the secondary DMMP-DAR, like the primary DAR, is also affected by DIMP. As can be seen in Table 1, when 0.1 gr*cm/liter of DIMP is inserted into the FOV, the net normalized signal produced by the third and fourth detectors now decreases by approximately 30% below the background DAR signal. By comparison, the secondary DAR output induced by 0.01 gr*cm/liter of DMMP is a positive 4.1%. Thus while the same quantity of DIMP was sufficient to nearly offset the signal of the primary DMMP DAR sensor, it is inducing a signal at the secondary DMMP DAR sensor that is distinguishable from the DMMP signal. This example demonstrates that two different optical densities of DMMP and DIMP, $d_{DMMP}$ and $d_{DIMP}$, produce two different responses at the two DAR sensors of the quadrant. In actual use and after calibration, these responses can provide the necessary terms for two independent algebraic equations that can be used to compute the optical densities of both species. Thus, even without a dedicated DAR sensor, DIMP can be detected and its optical density measured by a dual DMMP-DAR sensor. Independent confirmation of these measurements can be achieved by a third DIMP-DAR sensor consisting of a detector with a filter at 985 cm$^{31\ 1}$ at the strongest line of DIMP and one at 934 cm$^{-1}$ for background correction. Additional quadrant detectors with dedicated filters and BRDs can be added to the system for further specificity or to detect of additional target species. Alternatively, linear detector arrays with a linear filter array consisting of miniature filter elements can be designed and built for detection of these and additional target species and for correcting, background effects by additional atmospheric species. Commercially available linear arrays now include 256 elements, thereby allowing simultaneous detection of up to 128 different lines of target species and correction of one background effect for each species. The use of BRDs for each pair of detector elements in such large arrays simplifies considerably the data collection, storage and processing efforts.

Unlike the DAR, the NFCR sensor collects the background radiation at the frequency of the sample detector. Therefore, correction for background absorption and emission occurs simultaneously for all background species that affect the sample detector. In addition, since only one frequency range is included in the measurement, interference by one target species in the detection of another target species can occur only if their spectral lines overlap within the bands of the notch or bandwidth-limiting filters (e.g., filters 25 or 64 in FIGS. 1 and 2). This was demonstrated by computing the net NFCR signal of a DMMP-NFCR induced by 0.01 gr*cm/liter of DMMP. The design of this DMMP-NFCR included a notch filter at 1086 cm$^{-1}$ bandwidth of 12.6 cm$^{-1}$ and transmission of 0.3 and a bandwidth-limiting filter with bandwidth of 15 cm$^{-1}$ and transmission of 0.64. As before, data processing of two unitary (single element) detectors is best performed by a BRD connected to the sample and reference detectors. As shown in Table 1, the presence of DMMP in the FOV reduces the signal below its background by approximately 1.8%. When 0.1 gr*cm/liter of DIMP is introduced into the FOV instead, the net normalized DMMP NFCR signal increases by approximately 2.5% above the background. As with the DMMP-DAR sensor, DIMP may offset the signal induced by DMMP in a DMMP NFCR sensor when included as a mixture with DMMP. A second NFCR sensor such as a DIMP-NFCR is needed to overcome such ambiguity. When DIMP at its primary line is sensed by such a dedicated DIMP-NFCR sensor, the signal associated with the same DIMP optical density of 0.1 gr*cm/liter DIMP is 8.7% below background. Meanwhile, the signal induced by 0.01 gr*cm/liter of DMMP in the same sensor is only 0.16% above background. For this simulation, the DIMP NFCR sensor included a notch filter centered at 983 cm$^{-1}$ to coincide with its strongest line. The other parameters of the sensor were identical to those of the DMMP-NFCR sensor. Therefore, as with the DAR, sensing the same DMMP/DIMP mixture when detected by two separate NFCR sensors provides two markedly different responses.

By the use of calibrated response parameters for each of the species detected by each of the sensors, it is possible to solve algebraically the optical densities of both species even if they are present simultaneously in the FOV. Further confirmation of the measurement can be achieved by introducing NFCR sensor for the detection of the secondary line of DMMP, or one of the secondary lines of DIMP, or both Similarly to the DAR, the use of additional quadrant detectors or linear arrays may permit extension of the measurement to additional species.

Clearly, the NFCR can provide a specificity comparable to that of the DAR. However, the predicted residual background signal (not shown), even after correction, is higher than that of the DAR. In addition, notch filters currently are not available at all spectral regions. Although notch-like performance can be achieved by using bandpass filters as mirrors (e.g., as illustrated in FIG. 3), such an approach somewhat complicates the system design. Nevertheless, in applications such as hydrogen fire detection in the UV, the use of NFCRs may be preferred. There, the level of background radiation, primarily by daylight or sky light varies rapidly with wavelength due to stratospheric ozone absorption of solar radiation Thus the use of reference and sample detection at approximately the same frequency range simplifies and improves background correction.

TABLE 1

COMPARISON OF RESPONSES OF FOUR SENSORS TO PRESENCE OF DMMP AND DIMP IN THE FOV

| Detector Type | Detected Species | Optical Density (gr*cm/liter) | Net Normalized Signal Relative to Background |
|---|---|---|---|
| Primary DMMP-DAR | DMMP | 0.01 | 15.5% |
| Primary DMMP-DAR | DIMP | 0.1 | −10.1% |
| Second DMMP-DAR | DMMP | 0.01 | 4.1% |
| Second DMMP-DAR | DIMP | 0.1 | −30% |
| Primary DMMP-NFCR | DMMP | 0.01 | −1.78% |
| Primary DMMP-NFCR | DIMP | 0.1 | 2.5% |
| Primary DIMP-NFCR | DMMP | 0.01 | 0.16% |
| Primary DIMP-NFCR | DIMP | 0.1 | −8.7% |

Sensitivity of Measurements in the Far Infrared Using Cooled and Uncooled Filters To further illustrate the performance of the DAR system, its sensitivity in the fir infrared was evaluated. Two sources usually will limit the detection sensitivity of target agents by the DAR or NFCR systems of the present invention: detector noise as determined by the noise equivalent power (NEP) or the detectivity D*, and, for uncooled filters, thermal emission by the bandpass filters themselves, will appear as a large DC component that also carries its own shot-noise. With respect to the latter, this thermal emission can exceed significantly the transmitted irradiance when the filters are at room temperature. Although subtraction by the detector output comparison device of the reference photocurrent from the sample current will correct for that DC component, the shot-noise associated with it cannot be subtracted (in fact it is additive as root-mean-square (RMS)). That noise can be reduced by cooling the filters, thereby reducing their emission, or by a sufficiently long integration time. The analysis below considers separately the effects of detector noise and filter thermal emission, and provides an estimate of the overall SNR.

The procedure detailed in Flanigan, *Predication of the Limits of Detection of Hazardous Vapors by Passive Infrared With the Use of MODTRAN*, App. Opt. vol. 35, 6090–98 (1996), was used to estimate the detection limit of Fourier transform infrared spectrometer (FTIR) sensors based on their detector's NEP. The available signal is limited by the detection solid angle $\Omega$ and by the lens area A. These two parameters can be combined into a single parameter, the etandue (E), which for normal incidence can be expressed by:

$$E = (A\Omega) \approx \left(\frac{\pi d_d}{4f/\#}\right)^2 \qquad (2)$$

The second term in Equation 2 is an approximation of the etandue as derived using geometrical optics and includes the lens f/# and the diameter $d_d$ of the detector's active area. For a suggested f/1 lens and for a suggested $d_d$=0.3 cm, the etandue is E=0.056 sr-cm$^2$. Using this etandue, the noise equivalent spectral radiance (NESR) of an infrared detector can be specified by:

$$NESR = \frac{\sqrt{A_D/t}}{D * Et_s \bar{v}} \quad (3)$$

Where $A_D$ is the detector area, t=10 ms is a suggested detection integration time, $D^*=2.5 \cdot 10^8$ cm Hz$^{1/2}$/W$^{-1}$ is the detectivity of a potential thermopile ($D^*$ for pyroelectrics is similar), $\tau_s=0.64$ is the transmittance of a typical bandpass filter and $\Delta \bar{v}=15$ cm$^{-1}$ is its bandwidth. With these parameters, NESR=$1.98 \times 10^{-8}$ W/(cm$^2$-sr-cm$^{31}$ $^1$). For comparison, the spectral radiance ($L_{BB}$) at 1086 cm$^{-1}$ by a blackbody at 296° K. is:

$$L_{BB} = 4.21 \times 10^{-6} \ \frac{W}{cm^2 - sr - cm^{-1}} \quad (4)$$

Thus, by depending on thermal emission for measurement, a sensor having these properties can provide a signal-to-noise ratio (SNR) of:

$$SNR = \frac{4.21 \times 10^{-6}}{1.98 \times 10^{-8}} = 213 \quad (5)$$

This high SNR can partly be attributed to the broadband detection of $\Delta \bar{v}=15$ cm$^{-1}$. By comparison, the change in signal due to absorption by 16.6 ppm-m DMMP at a distance of 3 km is greater than 15% (the results for 1 km are shown in FIG. 6, wherein the effective bandwidth—which exceeds the specified bandwidth of the filter due to the tight focusing of the fast lens—was used, as in eqns.3–6), well above the SNR limit of the detector itself However, the primary limit in most IR sensing is imposed by the thermal emission of the filters themselves which may significantly exceed the emission by the target thereby saturating the amplifiers and preventing the detection of the small absorption induced by the target species.

The SNR associated with the thermal emission of the above-described bandpass filters can be estimated by calculating separately the irradiance transmitted by the filters and then the shot-noise by their own thermal emission. The radiant power transmitted by an IR filter can be obtained by integrating $L_{BB}$ over its tranmission band, the detection solid angle $\Omega$ (which is defined by the FOV) and the lens area of the telescope or other collecting optics. For a fast f/1 lens with a short focus of f=15 mm, for $d_d=3$ mm detector and for a $\Delta \bar{v}=15$ cm$^{-1}$ detection bandwidth the transmitted iradiance is:

$$I_T \approx (L_{BB})(\Omega)(A)(\Delta \bar{v}) = (4.21 \cdot 10^{-6})(0.031)(1.77)(15) = 3.47 \cdot 10^{-6} \ W \quad (6)$$

As before (see Eqn.3) the broadband detection of 15 cm$^{-1}$ by the DAR/BRD provides a large signal relative to that of narrowband detection.

The total irradiance emitted by the bandpass filter itself at a temperature of T=300° K. is unfiltered (unlike its transmission) and must be integrated over the entire spectrum. If the filter is pasted directly over the detector then its area is identical to that of the detector and it is fully visible. With a conservative emissivity of $\epsilon=0.5$, the radiative power emitted by the filter and falling on the detector is:

$$I_f = \epsilon \sigma T^4 A_D = (05)(5.6697 \cdot 10^{-12})(300^4)(0.071) = 1.63 \cdot 10^{-3} \ \frac{W}{cm^2} \quad (7)$$

where a is the Stephan-Boltzmann constant. Clearly, the filter emission is nearly 500 times larger than the signal itself (eqn. 4). However, with the BRD, that filter emission is subtracted before amplification to within one part in 10$^6$. Of course, the dynamic range of the selected detector must be at least 10$^6$ to match the performance of the BRD. However, this is possible by both thermopiles and pyroelectrics as well as by HgCdTe (MCT), near IR, visible and UV detectors. Thus, if the shot-noise associated with the filter emission is smaller than the attenuation of $I_T$, by absorption by the target species, then detection of small absorptions may be possible.

To determine the shot-noise associated with $I_F$ when detected by a thermopile (or by pyroelectrics) and its magnitude relative to $I_T$, both their currents, $j_F$ and $j_T$, were calculated using the parameters of an available thermopile. For example, for an internal resistance of $R_S=18$ k$\Omega$ and responsivity of r=15 V/W, the current $j_r$ detected for $I_T$ is:

$$j_r = (I_T)(r/R_S) = 2.9 \cdot 10^{-9} A \quad (8)$$

The current $j_r$ associated with $I_p$ is determined similarly by substituting $I_F$ for $I_T$. The SNR associated with these currents is:

$$SNR = \frac{(j_T)(t/e)}{\sqrt{(j_F)(t/e)}} = 622 \quad (9)$$

The numerator of Equation 9 represents the number of electrons available to the pre-amplifier whereas the denominator represents the shot-noise associated with $I_F$, e=$1.6 \cdot 10^{-19}$ C is the charge of an electron and t=10 ms is the suggested detection time. If both the sample and reference filters induce the same shot noise then the SNR of the correlation measurement, following subtraction of their radiance by the BRD, must decrease by $(2)^{1/2}$. Yet this is still higher than the SNR of Equation 5. Thus, the SNR of the system, after subtraction of the large background by the BRD, should be sufficient to detect variations of less than 1%, whereas at 3 km the variation of the net normalized signal by 16.6 ppm-m of DMMP is greater than 15%. Thus, detection at sensitivities much better than 15 ppm-m should be possible even without cooling the filters. Note that this high SNR would not be possible without the BRD circuit that allows subtraction of the filter emission before the amplification stage. With alternative signal processing, the large background would saturate the amplifiers thereby preventing the detection. Of course, by cooling the filters by 50° C. using a single stage thermoelectric cooler, a factor of ~2 reduction in the filter emission is possible.

Selection of Detectors for Far Infrared Operation

The sensor of the present invention may be configured to detect passively gaseous chemicals in the far infrared including, for explanation purposes only and without limitation, pollution (e.g., pesticides, $N_2O$, $NO_x$, CO), $CH_4$ and other hydrocarbons, $H_2O$, $CO_2$, $O_3$, and $CH_4$. The sensor may also be used to detect the OH molecule, which is an intermediate product in all hydrogen and hydrocarbon fires. Because OH in flames emits brightly both in the ultra-violet and the infrared regions, detection of its emission can provide warnings of the onset of fires that otherwise are invisible. Particular examples include fires that may occur during the launch of space vehicles or the operation of race cars.

Successful detection of many of these chemicals, as well as other potential target species, requires eared detectors with high responsivity and low NEP. To the inventor's knowledge, the most sensitive and quietest detector in the far infrared is the HgCdTe (MCT), which needs to be cooled cryogenically to 7720 K. It can operate either in the photocurrent or photovoltaic mode. It can be manufactured to have peak sensitivity at a wide range of IR wavelengths. For example, at a peak sensitivity of 10.5 $\mu$m (950 cm$^{-1}$) the detectivity is $D^* \approx 2.5 \times 10^{10}$ cm·Hz$^{1/2}$·W$^{-1}$. Maintaining the MCT at 77° K. is not convenient for handheld sensors and may not be possible due to the high energy demand of cryogenic cooling for long-term unattended operation. On the other hand, without cooling, its responsivity and detectivity in the 8–13.3 $\mu$m range are insufficient for sensitive detection. Accordingly, alternative uncooled IR detectors are preferable.

Each of the practical uncooled detectors currently available in the 8–13.3 $\mu$m range are essentially thermal detectors that sense slight increases in temperature induced by the incident infrared radiation. The major shortcomings of these detectors are lower detectivity and longer response time (about $2.5 \times 10^8$ cm Hz$^{1/2}$ W$^{-1}$ and 1 ms, respectively) relative to that of a typical MCT (about $2.5 \times 10^{10}$ cm HZ$^{1/2}$ W$^{-1}$ and <1 $\mu$s). However, since the effect of their inherent noise may be reduced by long integration (about 10 ms), their slow rise times and reduced detectivities will not present a significant disadvantage. Furthermore, the relatively broadband detection associated with this invention relative to the bandwidth of FTIR or etalon based sensors improves significantly the signal-to-noise ratio (see, e.g., Flanigan, "Vapor-Detection Sensitivity as a Function of Spectral Resolution for a Single Lorentzian Band," App. Opt., vol. 34, at 2636–39 (1995)) thereby partially compensating for the lower detectivity of uncooled IR detectors. Such detectors also should have a large aperture that in turn provide the large FOV that is necessary for large signals (of course, large FOV reduces imaging resolution and therefore imaging may come at reduced sensitivity). It is expected that an aperture of about 3 mm will be required to measure agents at optical densities of at least 15 ppm-m. Thus, micro-bolometers that have good detectivity of $D^* = 2.5 \times 10^9$ cm Hz$^{1/2}$ W$^{-1}$ but dimensions of 30–40 $\mu$m are unacceptable for high sensitivity detection while larger bolometers have significantly reduced sensitivity and therefore are not acceptable either.

Thermopiles and pyroelectric detectors are the most favored detectors for use in connection with several embodiments of the present invention, such as hand-held, unattended or remotely piloted vehicle (RPV) based sensors. Both types of detectors can operate uncooled, have an exceptionally broadband response (0.6–35$\mu$), with a long rise time (1–200 ms) and a large aperture (possibly greater than 5 mm). In addition, their low cost (about $40 for a thermopile and about $500 for a quadrant pyroelectric) makes it possible even now to combine several pairs of these detectors with their own BRDs for multiple-species sensing or for same-species multiple-line detection for added specificity or for multiple background species correction.

A thermopile generally consists of arrays of thermocouple junctions e.g., 72) connected in series to measure directly the temperature of a detecting surface relative to a heat sink that acts as a cold junction. The response is temperature dependent. Drifts in the heat sink temperature therefore may introduce an error. However, if the heat sinks of the two thermopiles that are used as a pair for the sensor are kept both at the same temperature (such as, for example, by physically connecting them with a good heat conductor), then drifts in that common temperature will be subtracted by the BRD or by other subtraction techniques used for this measurement and will not affect the measurement. The parameters of a commercially available thermopile (e.g., 3M™ model from Dexter Research Center, Inc.) include a detectivity of $D^* \approx 10^9$ cm Hz$^{1/2}$ W$^{-1}$, responsivity of 15 V/W and internal resistance of 18 K$\Omega$. With these parameters, target species detection at a 15 ppm-m level may be possible from distances of up to 3 km using filter bandwidths of about 13 cm$^-$ and transmissions of about 65%.

As previously noted, it is possible to integrate several detectors and a BRD assembly having a plurality circuits, with one or more sample detectors in the sample detector assembly being configured to sense a different target or group of targets, and one or more reference detectors in the reference detector assembly being configured to sense background radiation associated with different spectral lines of the same background species or with lines of other background species. The output of each sample sensor will be fed into the sample leg of one BRD, whereas the output of the reference detector(s) will be fed to the matched reference leg of that BRD. The bandpass or notch filters may be integrated with their respective thermopiles as windows thereby making the detectors compact and robust.

Pyroelectric detectors can be an alternative to thermopiles as uncooled detectors for infrared sensing. Although their detectivity is similar to that of thermopiles, pyroelectric detectors have a voltage responsivity of up to 900 V/W and internal resistance of up to $10^{11}\Omega$, which are significantly higher than those of thermopiles. Pyroelectrics accordingly offer lower Johnson noise and higher pre-amplified output, thus a better signal to noise ratio (SNR). Pyroelectrics consist of ferroelectric crystals (e.g., LiTaO$_3$) that contain bound ions that are positioned non-symmetrically. When the temperature changes, these ions shift slightly, thereby creating polarization currents within the lattice. As a result, pyroelectrics are sensitive only to the time derivative of the temperature (dT/dt).

When the temperature is steady and when staring at a stationary target, the pyroelectric signal fades away within few seconds. This property presents an advantage when detecting strong thermal emissions of nearby uncooled optical components or when the temperature of the detector itself cannot be controlled accurately. But to sense a stationary or slowly varying target, such as atmospheric pollution, the necessary transient must be created artificially by moving the sensor, or by modulating the incident radiation. With modulation in the 0.1–10 Hz range, a 5 mm LiTaO$_3$ detector can provide nearly uniform response with detectivity of $D^* = 4 \times 10^8$ cm Hz$^{1/2}$ W$^{-1}$. Furthermore, because of the subtraction-normalization process, whether using a BRD or another device for this purpose, moderate fluctuations in D* due to inconsistent modulation will be canceled out in real time, provided that they affect identically both the sample and reference detectors. Pyroelectrics are commercially packaged either as unitary 5 mm detectors or as 20 mm quadrant detectors (see, for example, FIG. 7). There, one or two of the quadrants may be used for background sensing and correction, and the remaining quadrants may be used to sense one or more different types of target species.

Imaging Target Species

The DAR and NFCR sensors of the present invention may be used for imaging (e.g., with a FPA) as well as for single point detection. They may be used in many forms including, for example, in simple handheld devices that can be pointed by the user towards a target area like a flashlight, in order to scan a broad area for one or more target agents or as a binocular with one "eye" comprising the sensor and the other "eye" comprising an ordinary telescope. Where the DAR or NFCR sensors of the present invention are embodied in handheld devices, it may be desirable that they utilize only unitary detectors (i.e., single pixel). Other applications, such as for delineating the edges of a chemical vapor cloud with a binocular-like device or a camera-like device, however, may benefit from imaging capabilities of FPAs or other imaging devices. Imaging is possible, for example, when the detection is by a FPA through the bandpass filters. The specificity of both the NFCR and DAR systems may be enhanced by replacing the single-band sample filter with a striped filter consisting of repeating sequence of a plurality of strips of bandpass (or notch) filters that are centered at the frequencies of the agents selected for detection. It will be appreciated that the use of the term "striped filter" is for ease of description only. Although it may be that a "striped filter" may be more economically manufactured in a stripe or strip format, it may also be made using a checker, concentric circle, honeycomb, or other suitable format. The term "striped filter" is intended to include any such format.

Figure 8B:
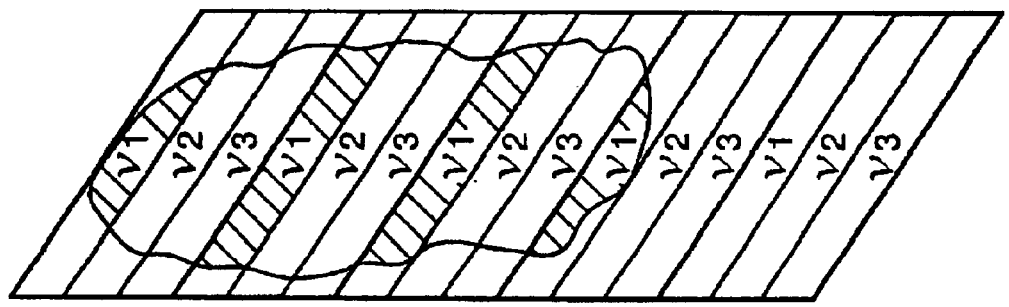
FIG. 8B is a schematic illustration of an image of a cloud of a target species as imaged using the striped filter configuration of FIG. 8A
Figure 8A:
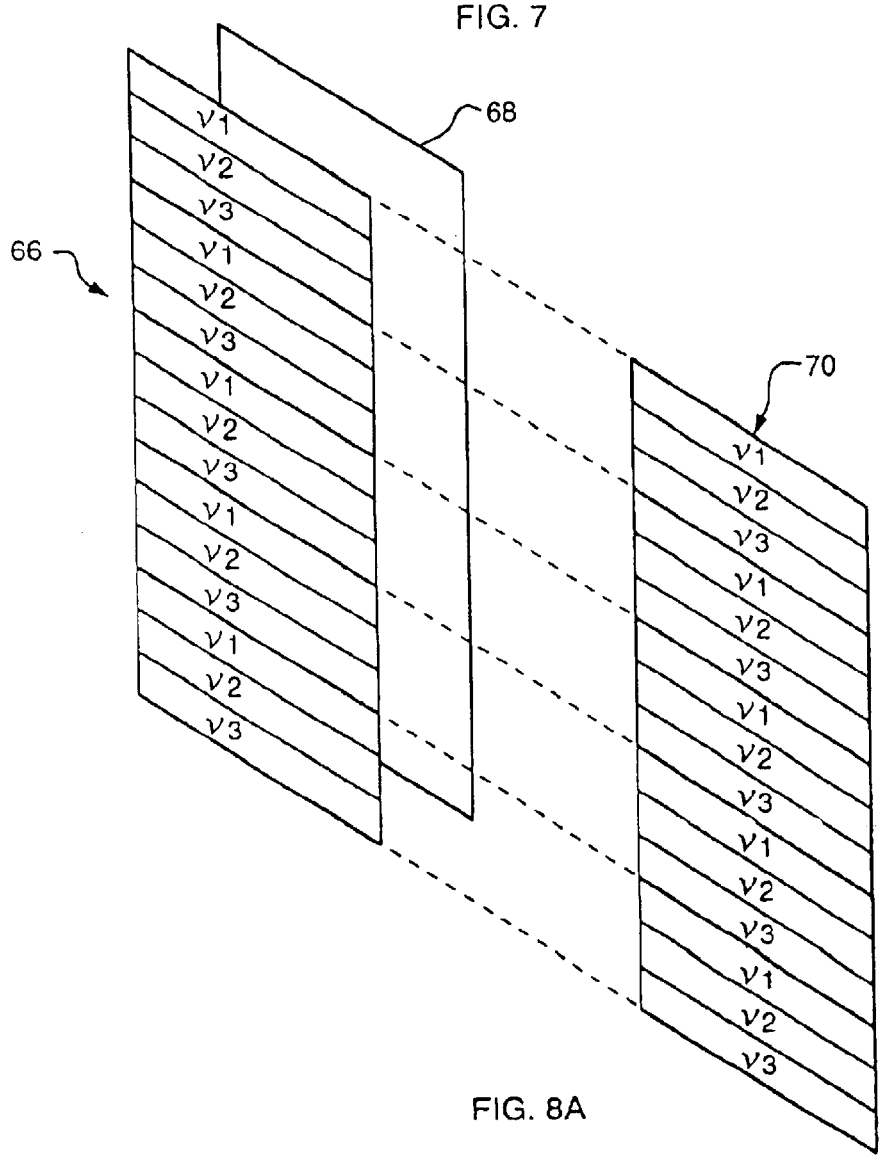
FIG. 8A is a schematic illustration of a striped filter configuration for multiple species detection using the sensor of the present invention.

FIG. 8A illustrates one possible configuration for a striped sample filter 66 having a sequence of three bandpass transmissions (or notches) centered at frequencies $v_1$, $v_2$ and $V_3$. The sequence is repeated through the entire filter. The detector 68 behind this filter is an FPA consisting of a number of pixels sufficient so that radiation passing through each of the filter strips illuminates several pixel rows. Similarly, the reference filter 70 of the DAR (or the bandwidth-limiting filter for the NFCR) consists of a repeating sequence of bandpass strips that match the strips of sample filter 66 for optimal background subtraction. Thus, for operation as a DAR, for example, the strips of reference filter 70 at $v_1'$, $V_2'$ and $v_3'$ are the frequencies of the bandpass transmissions that provide the optimal background subtraction for the species and their spectral lines that were selected for detection through the stripes of sample filter 66, whereas for the NFCR, these strips are the bandwidth limiting filters at $v_1$, $v_2$ and $v_3$ near detector 68.

FIG. 8B illustrates the possible image of a target agent cloud, such as a pesticide cloud, when imaged through this striped filter configuration. Although parts of the cloud that did not include absorption features at $v_2$ or $v_3$ remain invisible, its boundaries are well defined because the typical size of a plume exceeds significantly the imaging resolution. Effectively, the system as shown in FIGS. 8A and 8B is a multiplexed triple-channel sensor that trades part of the spatial resolution of the system for higher specificity. However, for further refinement of the lateral spatial distribution of the cloud and its depth, a companion system such as a DIAL or FTIR can further probe the image. Furthermore, in applications from moving vehicles, if the stripes of the proposed filters are oriented transversely to the vehicle path, continuous coverage can be achieved using the sensor in a "push-broom" mode.

By further adding strips to each sequence, additional specificity may be achieved. A "battery" of filter strips (bandpass or notch) matching 2–3 spectral lines of the same agent or lines of other agents may be used to positively detect any of those agents. The spectral separation of greater than 15 cm$^{-1}$ between adjacent features of the selected agents is sufficient to resolve them with such bandpass filters. Detection will be achieved when an agent is detected through at least one strip. Positive identification will be achieved by detection through two or more strips dedicated for that agent and not through strips dedicated to other agents. In addition, the magnitude of the net normalized signals obtained through the various strips of the filter can be used for positive identification of the agents.

An important part of this configuration is the accurate and reproducible spatial overlap between the images obtained through the strips of the sample and reference filters. Otherwise, subtraction of the background may not be complete or even may be exacerbated by subtraction of the "wrong" background. Using switching devices such as those described in connection with the present invention guaranties that after initial alignment of the filters among themselves and with the FPA, the alignment will be maintained during the switching cycles. In contrast to conventional systems, the approach of the present invention can double either the spatial resolution or the number of detectable species by dividing the detection into two paths.

Switching Devices

As previously stated, when employing an embodiment of the present invention such as that illustrated in FIG. 2, switching devices 54 and 56 may be required to selectively permit first and second portions 36 and 40 of beam 22 to reach detector 60. Until recently, switching between two filters was accomplished mechanically, e.g., by moving the filters themselves in front of the detector. But for imaging, the slight misalignments associated with such mechanical translation of the filters can introduce large errors due to loss of registration between the sample and reference images. A new technology introduced by NASA is described in U.S. Pat. No. 5,128,797 to Sachse, et al., discussed previously, which is incorporated herein by reference in its entirety. The switching design of the '797 patent eliminates all moving parts by using a polarization modulator and two polarization beam-splitters to optically switch between two paths, each containing a filter. Although a sensor could be produced using such a non-mechanical switching device that is capable of operation in the 3–5 μm range, the performance of available polarizing beam splitters in the 8–13.3 μm range presently may not be satisfactory to develop such a detector for use in the 8–13.3 μm range. The device also is undesirably complex and expensive.

The present invention therefore contemplates that for operation in the 8–13.3 μm range or other spectral ranges where the polarization modulator switching may not be possible, the switching device may instead comprise a simple, inexpensive mechanical shutter device. Such a device may include two asynchronous, electronically controlled mechanical-shutters 54, 56, one in each of first and second optical paths 38 and 40, or tuning fork shutters, to selectively switch viewing between these paths, thereby allowing independent imaging through first and second filters 44, 46. Although the switching rate of the mechanical shutters currently available is significantly lower than the switching rate of 40 kHz achieved by the design of the '797 patent, it can exceed the imaging rate of available FPAs (approximately about 50 Hz) thereby permitting full system performance. Alternatively, the switching devices may comprise slotted chopper wheels, which also are simple devices, have faster switching rates than shutters, and can be easily incorporated into a portable sensor. Like the polarization modulation approach, the use of asynchronous mechanical shutters 54, 56 does not affect the optical path alignment that is necessary for accurate image subtraction.

Selection of Light Collecting Optics

As previously indicated, the light collecting optics 22 or 32 used in connection with the sensor of the present invention may comprise one or more optical elements including, for example, lenses, holographic lenses, mirrors, optical fibers, optical filters, slits, apertures or the like. Preferably, the sensor of the present invention is constructed to be a highly portable device capable of operation in adverse environments. Accordingly, the non-imaging sensor may be constructed as a compact device having a rugged construction. To contribute to a compact constructior, the components of the sensor may be integrated. To contribute to a rugged construction, the collecting optics may include a non-fragile lens. Although the collecting optics preferably will provide excellent light gathering capabilities for non-imaging applications, it is not essential that the lens provide high imaging resolution. It preferably will provide a large etandue (Equation 2) which is achieved partly by a large $\Omega$. A large FOV, or $\Omega$, may be achieved by large $d_d$ or low f/#. A f/1 holographic lens with f=1.5 cm may enhance the etandue while at the same time having a moderate size and non-fragile construction for far infrared sensing. It can be developed by embossing its pattern on AMTIR-1 which transmits both in the 8–13.3 $\mu$m and the 3–5 $\mu$m ranges. The material is amorphous and non-fragile, available in 12"×18" sheets thereby allowing design of any reasonable aperture size. The hologram can be designed either to provide multiple focal spots—one for each detector—thus permitting imaging of the same target area on separate detectors. Alternatively, a single-focus lens will provide images on each of the detectors of slightly offset areas of the target. Other holographic lenses with similar properties may be constructed for other spectral ranges.

Energy and Cooling Requirements

In one embodiment, the sensor of the present invention is designed to be compact for handheld and possibly unattended applications and operate passively in the far infrared. Combined power demand for the thermopiles or \pyroelectrics, their amplifiers and a BRD assembly having one or more BRD circuits is on the order of 100 mW with a 12 V DC supply. A handheld sensor therefore may operate on a standard 12 V battery. For example, the 12 V Eveready Energizer™ alkaline battery can provide approximately 0.2 W-hour before its voltage declines below 11 V. Thus, with even 100 mW demand, continuous operation of 2 hrs is possible with a single 12 V battery.

If the temperature of the thermopile must be maintained steady, a power of 0.1 W may be required when using a solid-state Peltier effect thermoelectric cooler and with maximum temperature differential of $\Delta T=\pm 5°$ C. between the detector and its environment. This power can also be provided with that one 12 V battery of the handheld system with a lifetime of continuous operation of up to about 1 hr.

Although cooling of the optical filters is not likely to be necessary, as previously discussed, it may provide an advantage when high sensitivity is needed. The extent of heat transfer to the filters was estimated for a temperature differential of 50° C. across a silica powder/aluminum insulator with a conduction coefficient of k=0.0017 W/m K. The total heat transfer was found to result in a loss of only 0.2 W. A solid state thermoelectric cooler having a coefficient of performance of 0.05 thereby requiring 4 W can remove this heat. Short operation may be possible, for example, with larger battery packs or with rechargeable Li batteries.

Sensor Packaging

The sensor of the present invention may be packaged in any of a number of configurations. For example, it may be packaged as a handheld device, as an unattended ground or marine sensor, as a vehicle accessory, as part of the avionics of aircraft such as helicopters or RPVs, or as an unattended sensor for security, safety or compliance applications. It may also be hybridized with sensors of higher specificity to provide rapid scanning and detection-triggering capabilities. For example, the sensor may be integrated with a Fourier Transform Infrared Spectrometer (FTIR) system, a differential-absorption lidar (DIAL), or in-situ sensors such as an ion-mobility spectrometer (IMS) or sorbing sensor. In-situ sensors such as IMS or sorbing sensors are able to provide detection only at the point of measurement, thereby necessitating the collection and analysis of samples at numerous locations using a complex search pattern. However, by integrating such an in-situ sensor with the sensitive handheld remote sensor of the present invention, the search procedure may be significantly simplified and accelerated to provide coverage without gaps.

It is contemplated that the sensor of the present invention will be particularly useful for pollution and toxic agent detection. When packaged as a handheld sensor, it may, for example, be available to domestic rescue personnel in emergency operations. The handheld sensor in non-imaging applications may be configured generally in the shape of a gun, with an easily grippable handle and sight, as a binocular with one "eye" dedicated to sensing, or in any other useful configuration. As described, the sensor may be made to provide rapid detection and identification capabilities of several agents simultaneously by use of a plurality of detector pairs and BRDs or other data processing circuits. The operator may scan the target area by pointing the sensor to obtain wide coverage and to determine which areas are safe to enter.

As a ground sensor without any temperature control provisions and with certain battery packages, the sensor of the present invention may be designed to operate continuously for 30 days on a single battery charge while providing communication link with a central control center. Ground sensors may be designed for airdrop deployment or manual deployment to monitor compliance, covert activities or for advanced warning. As an airborne sensor, the sensor of the present invention may, for example, provide forward-looking warning capabilities for helicopter personnel. Similarly, when deployed on a RPV, the sensor may provide remote sensing capabilities beyond the nominal optical detection range of the sensor.

It will now be appreciated that the present invention provides a sensor and method for determining the presence or optical density C×L) of a target species, particularly in, but not limited to, the 8–13.3 $\mu$m range, which addresses several of the disadvantages of conventional sensors and sensing methods. The remote sensor of the present invention is simple, compact, energy efficient and easy to use. It also combines the advantages of being inexpensive, having a large FOV for non-imaging applications, and having a good specificity and resolution capability. The sensor also is well-suited for handheld, mobile or stand-alone operation for detecting and imaging gaseous chemicals such as pesticides, their precursors and reduced products, atmospheric effluents, hydrogen and hydrocarbon fires.

The sensor is also well suited for applications in the UV and visible range. For example, it can be configured as a DAR or NFCR for the detection of the emission of OH molecules in flames, thereby providing a simple remote sensor or remote imaging device of invisible or bluish flames such as the flames formed by hydrogen, methane, other light hydrocarbons or non-sooting flames. Applications may include safety devices for space launches, race cars, or pipe lines and refineries.

When configured as a DAR flame sensor, the sample filter 10 or 44 may have a transmission at about 308 nm and bandwidth of approximately 15 nm, where OH in flames has its strongest natural emission. This emission is well defined and it is formed as a spectral band that extends to approximately 320 nm. Thus, detection anywhere within this range through the sample filter can provide excellent signal that is directly associated with the chemical reaction in the flame and can be used to delineate it. Furthermore, because of the natural absorption of sunlight by ozone in the stratosphere, the intensity of daylight or skylight radiation at 308 nm is low, thereby providing very little background interference, even during daytime detection or when the sky is in the background. Reference filter 14 or 46 for this DAR application may be centered at 350 nm. There, the emission by OH is at least ten times lower than at 308 nm. Therefore, most of the radiation at that wavelength is from the background. Although the intensity of daylight or skylight is more than three times higher at 350 nm than at 308 nm, that difference can be partly compensated by selecting a reference filter 14 or 46 that has a bandwidth that is three times narrower than the sample filter.

When the sensor of the present invention is configured as a NFCR, a notch filter centered at 308 nm and a bandwidth of 15 nm may be used as the sample filter 10 or 44. A bandwidth-limiting filter 25 or 64 may be used, as previously discussed, with a line center also at 308 nm and bandwidth larger than 15 nm.

Both the DAR and NFCR configuration requires UV sensitive detectors. Unitary detectors 26 and 28 that are used for non-imaging applications include preferably photomultiplier tubes (PMTs) with UV sensitive photo-cathodes. Such PMTs are available in many configurations from several manufacturers. New types of solid state sensors with UV sensitivity are now also becoming available and may also be used.

For imaging applications, the flame sensing DAR or NFCR can be configured as shown in FIG. 2 using the switching device described in the '797 patent. In both case, detector 60 may included an UV sensitive CCD array or UV sensitive intensified CCD array or other similar UV sensitive imaging device including photographic material.

It is believed that the many advantages of the present invention will now be apparent to those skilled in the art. It will also be apparent that a number of variations and modifications may be made thereto without departing from its spirit and scope. Accordingly, the foregoing description is to be construed as illustrative only, rather than limiting. The present invention is limited only by the scope of the following claims.

I claim:

1. A remote sensor comprising:

a first optical path and a second optical path;

light collecting optics configured to collect light or other radiation to be transmitted along said first and second optical paths;

a sample filter assembly positioned in said first optical path after said light collecting optics;

a sample detector assembly positioned in said first optical path after said sample filter assembly, and a reference detector assembly positioned in said second optical path after said light collecting optics;

a reference filter assembly positioned in said second optical path between said light collecting optics and said reference detector assembly; and a detector output comparison device.

2. The remote sensor of claim 1, wherein:

said sample filter assembly comprises a bandpass filter and provides a sample output;

said reference filter assembly comprises a bandpass filter and provides a reference output; and said detector output comparison device comprises noise cancellation circuitry.

3. The remote sensor of claim 2, wherein:

said sample filter is configured to transmit at a frequency that coincides with a spectral line of a target species, said frequency also coinciding with a first spectral line of a non-target species; and said reference filter is configured to transmit at a frequency that coincides with said first spectral line of said non-target species, or a second spectral line of said non-target species, and which provides a magnitude of absorption or emission of said non-target species that is the same as, or comparable in magnitude to, the magnitude of absorption or emission of said non-target species provided by said frequency of said sample filter.

4. The remote sensor of claim 3, wherein said reference filter is configured to transmit at a frequency that coincides with a spectral line of a dust, aerosol, or atmospheric gas that is selected from the group consisting of $H_2O$, $CO_2$, $O_3$, $N_2O$, $NO_x$, and CO gases.

5. The remote sensor of claim 3, wherein said target species is selected from the group consisting of $CO_2$, $O_3$, hydrocarbons, $N_2O$, $NO_x$, CO, pesticides, chemical warfare agents, plasmas, electrical discharges, OH, and solid or liquid interfaces.

6. The remote sensor of claim 3, wherein a bandpass filter assembly is positioned in said first and second optical paths before said sample and reference detector assemblies to reduce background radiation passed by said sample and reference filter assemblies.

7. The remote sensor of claim 2, wherein said sample filter assembly comprises a first striped filter comprising a repeating sequence of a plurality of filters, and said reference filter assembly comprises a second striped filter comprising a repeating sequence of a plurality of filters.

8. The remote sensor of claim 7, wherein said plurality of filters of said first striped filter comprise are in the form of concentric circles.

9. The remote sensor of claim 7, wherein said plurality of filters of said first striped filter and said plurality of filters of said second striped filter comprise a plurality of matched filter pairs, and said sample and reference detector assemblies comprise a plurality of detector pairs corresponding to said plurality of matched filter pairs.

10. The remote sensor of claim 1, wherein said sample filter assembly comprises a notch filter and provides a sample output.

11. The remote sensor of claim 10, further comprising a reference filter assembly positioned in said second optical path between said light collecting optics and said reference detector, said reference filter assembly comprising a notch filter and providing a reference output, wherein said detector output comparison device compares said sample and reference outputs.

12. The remote sensor of claim 10, further comprising a blank positioned in said second optical path between said light collecting optics and said reference detector assembly.

13. The remote sensor of claim 12, further comprising a bandpass filter positioned in said first optical path before said sample filter, said bandpass filter having a frequency center that coincides with said attenuation frequency of said sample filter.

14. The remote sensor of claim 13, wherein said sample filter assembly comprises a striped filter comprising a repeating sequence of a plurality of filters.

15. The remote sensor of claim 1, wherein said remote sensor is configured for use as a handheld remote sensor.

16. The remote sensor of claim 15, wherein said handheld device has the shape of a gun.

17. The remote sensor of claim 15, wherein said handheld device is configured as a camera.

18. The remote sensor of claim 1, wherein said remote sensor is configured for unattended operation.

19. The remote sensor of claim 1, wherein said remote sensor is configured for operation in a remotely piloted vehicle.

20. A remote sensor comprising:
    a first optical path and a second optical path;
    light collecting optics configured to collect light or other radiation;
    a first beam splitter configured to transmit a first portion of the light or other radiation along a first optical path and to reflect a second portion of the light or other radiation along a second optical path;
    a sample filter assembly positioned in said first optical path after said first beam splitter;
    a detector assembly positioned after said sample filter assembly;
    means for directing said first and second portions of the light or other radiation to said detector assembly, said detector assembly being configured to detect a sample signal when said first portion of the light or other radiation reaches said detector assembly and to detect a reference signal when said second portion of the light or other radiation reaches said detector assembly; and
    a detector output comparison device positioned after said detector assembly.

21. The remote sensor of claim 20, wherein said detector output comparison device subtracts and normalizes said sample and reference signals.

22. The remote sensor of claim 21, wherein said detector assembly comprises two detectors.

23. The remote sensor of claim 22, wherein said detector output comparison device comprises a digital computer.

24. The remote sensor of claim 20, further comprising a reference filter assembly, and wherein:
    said sample filter assembly comprises a bandpass filter and provides a sample output signal; and
    said reference filter assembly comprises a bandpass filter and provides a reference output signal;
    wherein said detector output comparison device compares said sample and reference output signals.

25. The remote sensor of claim 24, wherein:
    said sample filter assembly is configured to transmit at a frequency that coincides with a spectral line of a target species, said frequency also coinciding with a first spectral line of a non-target species;
    said reference filter assembly is configured to transmit at a frequency that coincides with said first spectral line of said non-target species, or a second spectral line of said non-target species, and which provides a magnitude of absorption or emission of said non-target species that is the same as, or comparable in magnitude to, the magnitude of absorption or emission of said non-target species provided by said frequency of said sample filter assembly; and
    wherein said detector output comparison device subtracts said sample output signal and said reference output signal to minimize effects of said background radiation.

26. The remote sensor of claim 24, wherein said reference filter is configured to transmit at a frequency that coincides with a spectral line of a dust, aerosol, or atmospheric gas that is selected from the group consisting of $H_2O$, $CO_2$, $O_3$, $N_2O$, $NO_x$, and CO gases.

27. The remote sensor of claim 24, wherein said target species is selected from the group consisting of $CO_2$, $O_3$, hydrocarbons, $N_2O$, $NO_x$, CO, pesticides, chemical warfare agents, plasmas, electrical discharges, OH, and solid or liquid interfaces.

28. The remote sensor of claim 24, wherein a bandpass filter assembly is positioned in said first and second optical paths before said detector assembly to reduce background radiation passed by said sample and reference filter assemblies.

29. The remote sensor of claim 24, wherein said sample filter assembly comprises a first striped filter comprising a repeating sequence of a plurality of filters, and said reference filter assembly comprises a second striped filter comprising a repeating sequence of a plurality of filters.

30. The remote sensor of claim 29, wherein said detector assembly comprises a linear array of detectors.

31. The remote sensor of claim 29, wherein said detector assembly comprises a two dimensional array of detectors.

32. The remote sensor of claim 24, wherein said sample filter assembly comprises a plurality of bandpass filters and said reference filter assembly comprises a plurality of bandpass filters.

33. The remote sensor of claim 20, wherein said sample filter assembly comprises a notch filter and provides a sample output signal.

34. The remote sensor of claim 33, further comprising a reference filter assembly positioned in said second optical path between said light collecting optics and said detector assembly, said reference filter assembly comprising a notch filter and providing a reference output signal, wherein said detector output comparison device compares said sample and reference output signals.

35. The remote sensor of claim 33, wherein a bandpass filter assembly is positioned before said sample and reference detector assemblies to reduce background radiation passed by said sample and reference filter assemblies.

36. The remote sensor of claim 20, further comprising a blank positioned in said second optical path between said light collecting optics and said detector assembly.

37. The remote sensor of claim 33, wherein said sample filter assembly comprises a striped filter comprising a repeating sequence of a plurality of filters.

38. The remote sensor of claim 33, wherein said sample filter assembly comprises a plurality of notch filters.

39. The remote sensor of claim 33, wherein said remote sensor is configured as binoculars.

40. The remote sensor of claim 33, wherein said remote sensor is configured as a headset.

41. The remote sensor of claim 33, wherein said remote sensor is configured for operation in an aircraft.

42. The remote sensor of claim 20, wherein said detector assembly comprises a single detector, and said means for directing the first and second portions of the light or other radiation to said detector assembly comprises a means for alternately directing the first and second portions of the light or other radiation to said single detector.

43. The remote sensor of claim 42, wherein said means for directing the first and second portions of the light or other radiation to said detector assembly further comprises a mechanical switching device.

44. The remote sensor of claim 43, wherein said mechanical switching device comprises a slotted chopper wheel device.

45. The remote sensor of claim 43, wherein said mechanical switching device comprises a mechanical shutter device.

46. The remote sensor of claim 42, wherein said means for directing the first and second portions of the light or other radiation to said detector assembly further comprises a first mirror positioned in said first optical path after said sample filter assembly, and a second mirror positioned in said second optical path after said reference filter assembly, said first and second mirrors being positioned to direct the first and second portions of the light or other radiation to a second beam splitter, said second beam splitter being configured to recombine the first and second portions of the light or other radiation.

47. The remote sensor of claim 20, wherein said detector assembly comprises a detector selected from the group consisting of infrared detectors, infrared focal plane arrays, photo-diodes, avalanche-photo-diodes, photomultiplier tubes, semiconductor detectors, thermal detectors, charge-coupled devices, linear-diode arrays, and linear-detector arrays.

48. The remote sensor of claim 20, wherein said detector assembly comprises a focal plane array.

49. The remote sensor of claim 20, wherein said light collecting optics comprise a holographic lens.

50. The remote sensor of claim 20, wherein said memory device comprises a computer.

51. The remote sensor of claim 20, wherein said sensor is capable of operating on a 12 volt DC power supply.

52. A method of determining the presence of a target species, said method comprising:
receiving light or other radiation that has been absorbed by, or that has been emitted from, a target species;
directing a first portion of said light or other radiation through a sample filter assembly, and directing a second portion of said light or other radiation through a reference filter assembly;
directing said first portion from said sample filter assembly to a detector assembly, and directing said second portion from said sample filter assembly to said detector assembly;
detecting the power of said first portion of said filtered light or other radiation and the power of said second portion of said filtered light or other radiation using said detector assembly; and
comparing and normalizing said sample signal to said reference signal to produce a signal which is indicative of the absorption or emission of said light or other radiation by the target species.

53. The method of claim 52, wherein said step of receiving light or other radiation comprises receiving light from an artificial light source.

54. The method of claim 52, wherein said step of directing said first portion of said light or other radiation through a sample filter assembly, and directing said second portion of said light or other radiation through a reference filter assembly, comprises:
directing said first portion of said light or other radiation through a sample bandpass filter configured to transmit at a frequency that coincides with a first spectral line of the target species, said frequency also coinciding with a first spectral line of a non-target species; and
directing said second portion of said light or other radiation through a reference bandpass filter configured to transmit at a frequency that coincides with said first spectral line of said non-target species, or a second spectral line of said non-target species, and which provides a magnitude of absorption or emission of said non-target species that is the same as, or comparable in magnitude to, the magnitude of absorption or emission of said non-target species provided by said frequency of said sample bandpass filter.

55. The method of claim 54, wherein said step of directing said second portion of said light or other radiation through a reference bandpass filter configured to transmit at a frequency that coincides with a spectral line of a non-target species comprises directing said second portion of said light or other radiation through a reference bandpass filter configured to transmit at a frequency that coincides with a spectral line of an atmospheric gas that is selected from the group consisting of $H_2O$, $CO_2$, $O_3$, $N_2O$, $NO_x$, and CO gases.

56. The method of claim 54, wherein said step of receiving light or other radiation that has been absorbed by, or that has been emitted from, a target species, comprises receiving light or other radiation that has been absorbed by, or that has been emitted from, a target species selected from the group consisting of $CO_2$, $O_3$, hydrocarbons, $N_2O$, $NO_x$, CO, pesticides, chemical warfare agents, plasmas, electrical discharges, OH, and solid or liquid interfaces.

57. The method of claim 52, wherein said step of directing said first portion of said light or other radiation through a sample filter assembly, and directing said second portion of said light or other radiation through a reference filter assembly, comprises directing said first portion of said light or other radiation through a notch filter configured to attenuate at a frequency that coincides with a spectral line of the target species, and directing said second portion of said light or other radiation through a notch filter configured to provide no attenuation.

58. The method of claim 52, wherein said step of directing a first portion of said light or other radiation through a sample filter assembly, and directing a second portion of said light or other radiation through a reference filter assembly, comprises splitting said light or other radiation into a first portion and a second portion and directing said first portion along a first optical path and said second portion along a second optical path.

59. The method of claim 58, wherein said step of directing said first portion of said filtered light or other radiation to said detector assembly comprises using a switching device which selectively permits said first portion to reach said detector assembly while preventing said second portion of said filtered light or other radiation from reaching said detector assembly.

60. The method of claim 59, wherein said step of directing said first portion of said filtered light or other radiation to said detector assembly comprises using a switching device, comprises using a mechanical shutter device.

61. The method of claim 59, wherein said step of directing said first portion of said filtered light or other radiation to said detector assembly comprises using a switching device, comprises using a slotted chopper wheel device.

62. The remote sensor of claim 10, wherein said reference filter assembly comprises a blank.

* * * * *